US012183448B2

(12) United States Patent
Ichikawa

(10) Patent No.: US 12,183,448 B2
(45) Date of Patent: Dec. 31, 2024

(54) MEDICAL IMAGE PROCESSING APPARATUS, TROCAR, MEDICAL OBSERVATION SYSTEM, IMAGE PROCESSING METHOD, AND COMPUTER READABLE RECORDING MEDIUM

(71) Applicant: Sony Olympus Medical Solutions Inc., Tokyo (JP)

(72) Inventor: Kiyoshi Ichikawa, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 929 days.

(21) Appl. No.: 17/183,373

(22) Filed: Feb. 24, 2021

(65) Prior Publication Data

US 2021/0295980 A1    Sep. 23, 2021

(30) Foreign Application Priority Data

Mar. 18, 2020 (JP) .................................. 2020-048140
Dec. 24, 2020 (JP) .................................. 2020-215825

(51) Int. Cl.
| | |
|---|---|
| *A61B 5/05* | (2021.01) |
| *A61B 17/34* | (2006.01) |
| *A61B 90/00* | (2016.01) |
| *G16H 30/40* | (2018.01) |
| *A61B 17/00* | (2006.01) |

(52) U.S. Cl.
CPC .............. *G16H 30/40* (2018.01); *A61B 17/34* (2013.01); *A61B 90/37* (2016.02); *A61B 2017/00119* (2013.01); *A61B 2562/0247* (2013.01)

(58) Field of Classification Search
CPC .......... A61B 90/37; A61B 2017/00119; G16H 30/40
See application file for complete search history.

(56) References Cited

U.S. PATENT DOCUMENTS

2019/0125459 A1*  5/2019  Shelton, IV ........... G16H 40/63

FOREIGN PATENT DOCUMENTS

| JP | 2004290380 A | 10/2004 |
|---|---|---|
| JP | 2005021353 A | 1/2005 |
| JP | 2005211531 A | 8/2005 |
| JP | 2009273883 A | 11/2009 |
| JP | 2011024823 A | 2/2011 |
| JP | 2011194165 A | 10/2011 |

\* cited by examiner

*Primary Examiner* — Joel F Brutus
(74) *Attorney, Agent, or Firm* — XSENSUS LLP

(57) ABSTRACT

A medical image processing apparatus includes a control unit configured to cause, based on a detection result of at least one trocar into which a medical instrument is inserted, the at least one trocar being configured to detect a first state and a second state, the first state and the second state indicating an insertion state of the medical instrument into a subject, a display device to display at least one of a first image generated by capturing an image of an observation object inside the subject and a second image of the observation object inside the subject, the second image being previously acquired.

20 Claims, 14 Drawing Sheets

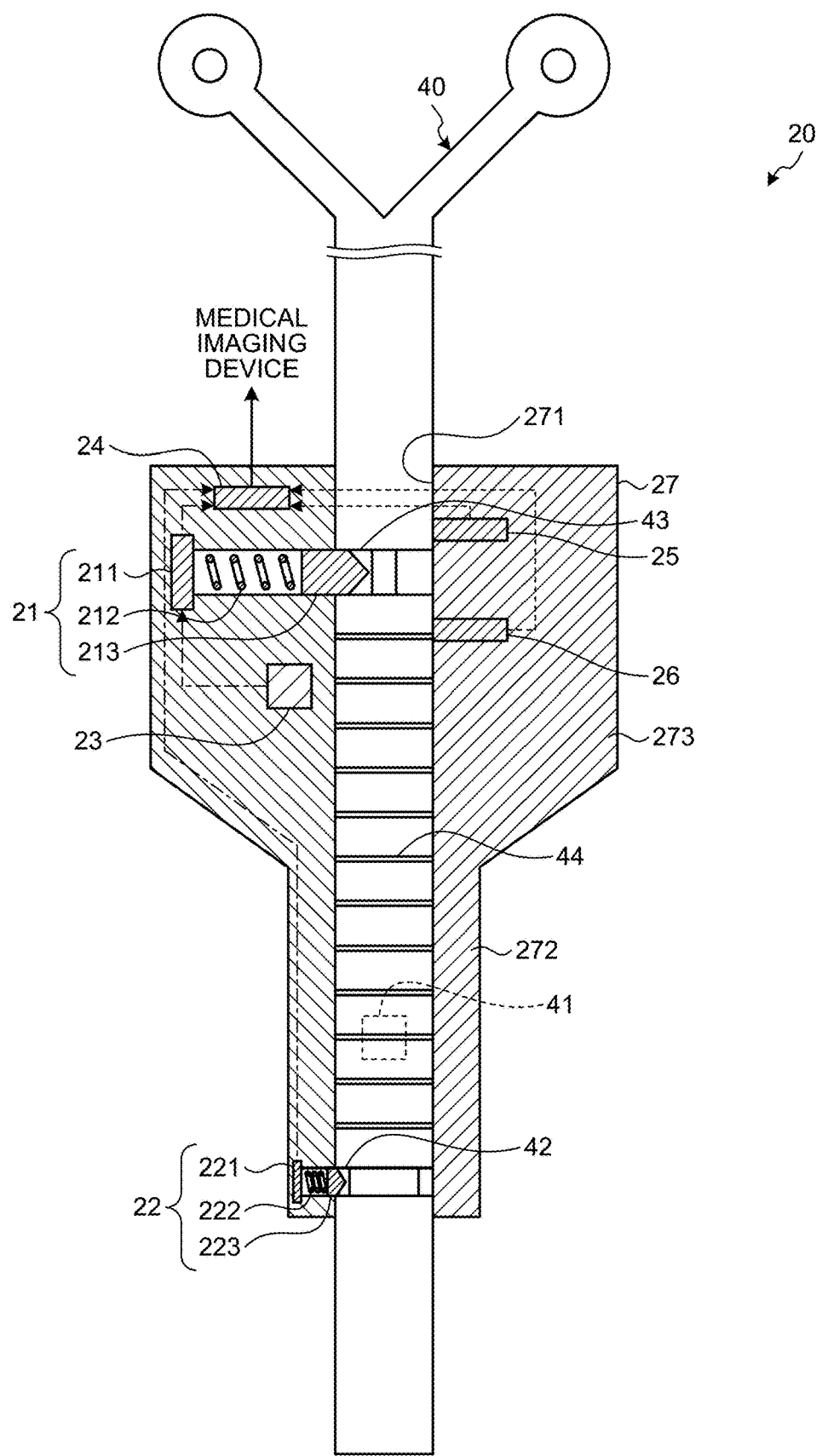

MEDICAL IMAGE PROCESSING APPARATUS, TROCAR, MEDICAL OBSERVATION SYSTEM, IMAGE PROCESSING METHOD, AND COMPUTER READABLE RECORDING MEDIUM

CROSS-REFERENCE TO RELATED APPLICATIONS

This application claims priority from Japanese Application No. 2020-048140, filed on Mar. 18, 2020 and Japanese Application No. 2020-215825, filed on Dec. 24, 2020, the contents of each are incorporated by reference herein in its entirety.

BACKGROUND

The present disclosure relates to a medical image processing apparatus, a trocar, a medical observation system, an image processing method, and a computer readable recording medium.

There is known a technique that displays an image obtained through, for example, CT and MRI in a superimposed manner on the affected part of a patient measured by a motion capture device in a surgical system (e.g., refer to JP 2016-158911 A). In this technique, reflected light from a plurality of markers disposed at predetermined intervals on the patient is received by each of motion capture devices, and an image to be displayed in a superimposed manner on the affected part of the patient is changed according to the coordinate position of a plurality of marker groups and the rotation amount of the marker groups.

SUMMARY

When an operator makes an approach to a surgical site during surgery, the operator performs incision while checking important blood vessels and nerves to be marks. However, in a technique involving a difficult approach, in an area that the operator may not observe in a computed tomography (CT) image or a magnetic resonance imaging (MRI) image which is checked before surgery, the shape and the position of a site checked after opening the abdomen of the patient are deviated from those in the CT image or the MRI image, which makes it difficult for the operator to instantaneously find the marks.

Further, in JP 2016-158911 A described above, the CT image or the MRI image is merely superimposed, there are problems in that a state in the image is deviated from an actual state of the patient, and the superimposed image becomes an obstruction.

There is a need for a medical image processing apparatus, a trocar, a medical observation system, an image processing method, and a computer readable recording medium that are capable of supporting an operator during surgery without disturbing the operator during the surgery.

According to one aspect of the present disclosure, there is provided a medical image processing apparatus including a control unit configured to cause, based on a detection result of at least one trocar into which a medical instrument is inserted, the at least one trocar being configured to detect a first state and a second state, the first state and the second state indicating an insertion state of the medical instrument into a subject, a display device to display at least one of a first image generated by capturing an image of an observation object inside the subject and a second image of the observation object inside the subject, the second image being previously acquired.

BRIEF DESCRIPTION OF THE DRAWINGS

FIG. 4E is a sectional view schematically illustrating a detection state of the medical instrument inserted into the trocar according to the first embodiment;

DETAILED DESCRIPTION

Hereinbelow, embodiments of the present disclosure will be described in detail with reference to the drawings. Note that the present disclosure is not limited to the embodiments described below. Further, in the following description, each drawing to be referred to merely schematically illustrates shape, size, and positional relationship to an extent that enables the details of the present disclosure to be understandable. That is, the present disclosure is not limited only to the shape, size, and positional relationship illustrated in each drawing. Moreover, identical parts are designated by identical reference signs throughout the drawings for description. Furthermore, an endoscope system using a laparoscope will be described as an example of the medical observation system according to the present disclosure.

First Embodiment

Schematic Configuration of Medical Observation System

Figure 1:
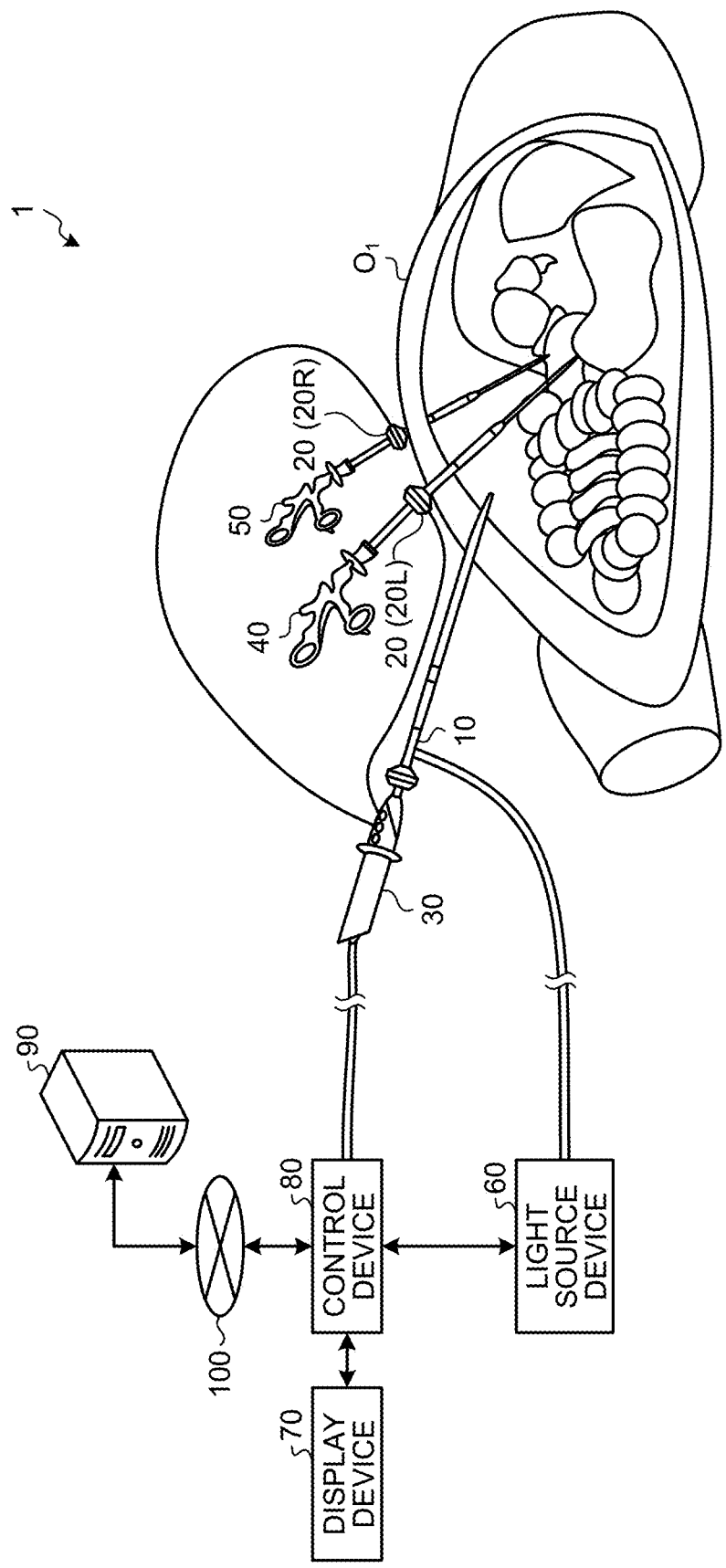
FIG. 1 is a diagram illustrating a schematic configuration of a medical observation system according to a first embodiment.

FIG. 1 is a diagram illustrating a schematic configuration of a medical observation system according to a first embodiment. A medical observation system 1 illustrated in FIG. 1 is a system used in the medical field, specifically, in a laparoscopic surgery. In the laparoscopic surgery, a plurality of holes are formed on the abdomen of a subject $O_1$ such as a human or an animal using trocars, and observation and procedures are performed while inserting a medical imaging device (a videoscope such as a rigid endoscope) and medical instruments such as forceps and an energy device such as an electric scalpel into the subject $O_1$ with the abdomen of the subject $O_1$ inflated with, for example, carbon dioxide. Note that although three holes are formed on the subject $O_1$ in FIG. 1, the number of holes may be appropriately changed according to an operative method or a technique.

The medical observation system 1 illustrated in FIG. 1 includes a trocar 10, a plurality of trocars 20, a medical imaging device 30, a medical instrument 40, a medical instrument 50, a light source device 60, a display device 70, a control device 80, and an image server 90.

The trocar 10 has a tubular shape and is inserted into the subject $O_1$. The medical imaging device 30 (described below) is inserted into the trocar 10. The trocar 10 is inserted into the umbilicus of the $O_1$. Note that, in the first embodiment, the trocar 10 includes a supply port (not illustrated) through which, for example, carbon dioxide for inflating the abdomen of the subject $O_1$ is supplied, and carbon dioxide supplied from the outside is supplied into the abdomen of the subject $O_1$ through the supply port.

The trocars 20 have a tubular shape and are inserted into the subject $O_1$. Either the medical instrument 40 or the medical instrument 50 (described below) is inserted into each of the trocars 20. In the following description, the trocar 20 into which the medical instrument 40 is inserted is represented as a trocar 20L, and the trocar 20 into which the medical instrument 50 is inserted is represented as a trocar 20R. Further, when either the trocar 20L or the trocar 20R is referred to, the trocar referred to is merely represented as the trocar 20.

The medical imaging device 30 is inserted into the subject $O_1$ through the trocar 10, generates image data by capturing an image of an observation object inside the subject $O_1$, and outputs the image data to the control device 80.

The medical instrument 40 is inserted into the subject $O_1$ through the trocar 20L. An operator such as a doctor operates the medical instrument 40 to perform procedures on the observation object. Examples of the medical instrument 40 include a syringe, forceps, a knife, a high-frequency snare, a treatment tool, and energy devices such as a high-frequency scalpel and an electric scalpel.

The medical instrument 50 is inserted into the subject $O_1$ through the trocar 20R. The operator operates the medical instrument 50 to perform procedures on the observation object. Examples of the medical instrument 50 include a syringe, forceps, a knife, a high-frequency snare, a treatment tool, and energy devices such as a high-frequency scalpel and an electric scalpel.

The light source device 60 applies illumination light to the observation object of the subject $O_1$ via the medical imaging device 30 under control of the control device 80. The light source device 60 supplies, as the illumination light, any one of while light, special light, and multi-spectral light to the medical imaging device 30 via, for example, a light guide. Here, the special light is excitation light or narrow-band light having a predetermined wavelength band. For example, the excitation light has a wavelength band of 400 nm to 430 nm (the center wavelength is 415 nm). On the other hand, the narrow-band light includes light having a wavelength band of 400 nm to 430 nm (the center wavelength is 415 nm) and light having a wavelength band of 530 nm to 550 nm (the center wavelength is 540 nm). Further, the multi-spectral light includes at least a wavelength band of light that enables discrimination of a living tissue, for example, an organ for each reflection frequency. For example, in the case of the pancreas, the reflection frequency is 16712 nm. The light source device 60 is implemented using, for example, a light source such as a white light emitting diode (LED), a red LED, a blue LED, a green LED, a purple LED, or an orange LED, a semiconductor laser, a rotary filter including a transmission filter that transmits light in a predetermined wavelength band, and a condenser lens.

The display device 70 displays an image input from the control device 80 under control of the control device 80. The display device 70 is implemented using, for example, a liquid crystal display or an organic electroluminescent (EL) display, and a sound speaker.

The control device 80 controls each unit of the medical observation system 1. The control device 80 performs various image processing operations on image data input from the medical imaging device 30 and outputs the image data to the display device 70 to cause the display device 70 to display the image data. Further, the control device 80 acquires, from the image server 90 via a network 100, simulation image data configured using three-dimensional image data, MRI image data, and CT image data which are previously acquired for the subject $O_1$ as a patient, performs various image processing operations on the acquired simulation image, and outputs the simulation image to the display device 70 to cause the display device 70 to display the simulation image. The control device 80 is implemented using a memory, and a processor including hardware such as a central processing unit (CPU), a graphics processing unit (GPU), and a field-programmable gate array (FPGA). Note that, in the first embodiment, the control device 80 functions as the medical image processing apparatus.

The image server 90 transmits the simulation image data requested from the control device 80 via the network 100. The image server 90 records, for example, two-dimensional image data or three-dimensional image data of each of patients acquired through, for example, CT or MRI, and simulation image data based on the two-dimensional image data or the three-dimensional image data. The image server 90 is implemented using a memory, a processor including hardware such as a CPU, a GPU, and an FPGA, and a recording medium such as a hard disk drive (HDD) and a solid state drive (SSD).

Functional Configuration of Principal Part of Medical Observation System

Figure 2:
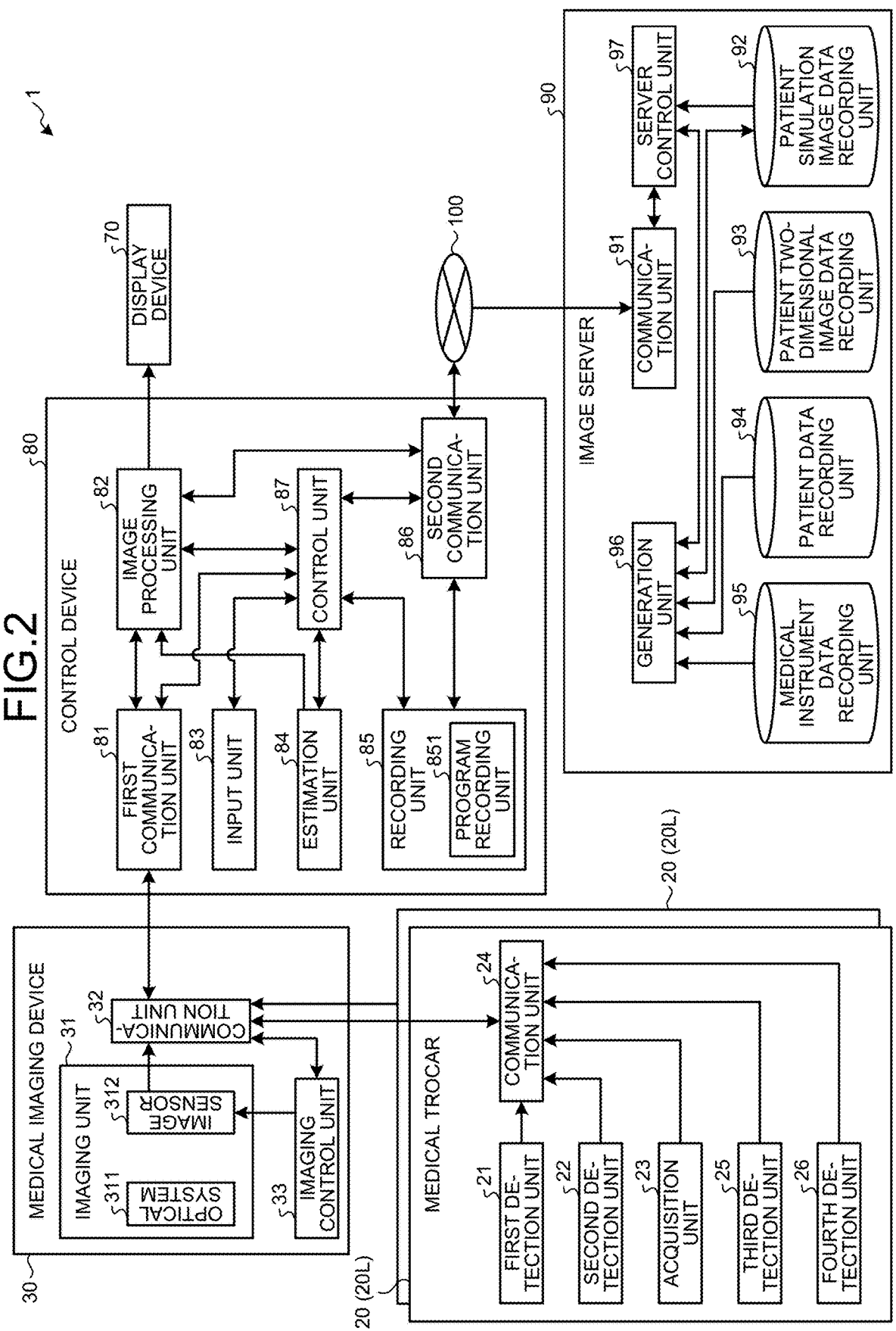
FIG. 2 is a block diagram illustrating a functional configuration of a principal part of the medical observation system according to the first embodiment.

Next, a functional configuration of a principal part of the medical observation system 1 described above will be described. FIG. 2 is a block diagram illustrating the functional configuration of the principal part of the medical observation system 1.

Configuration of Trocar

Figure 3:
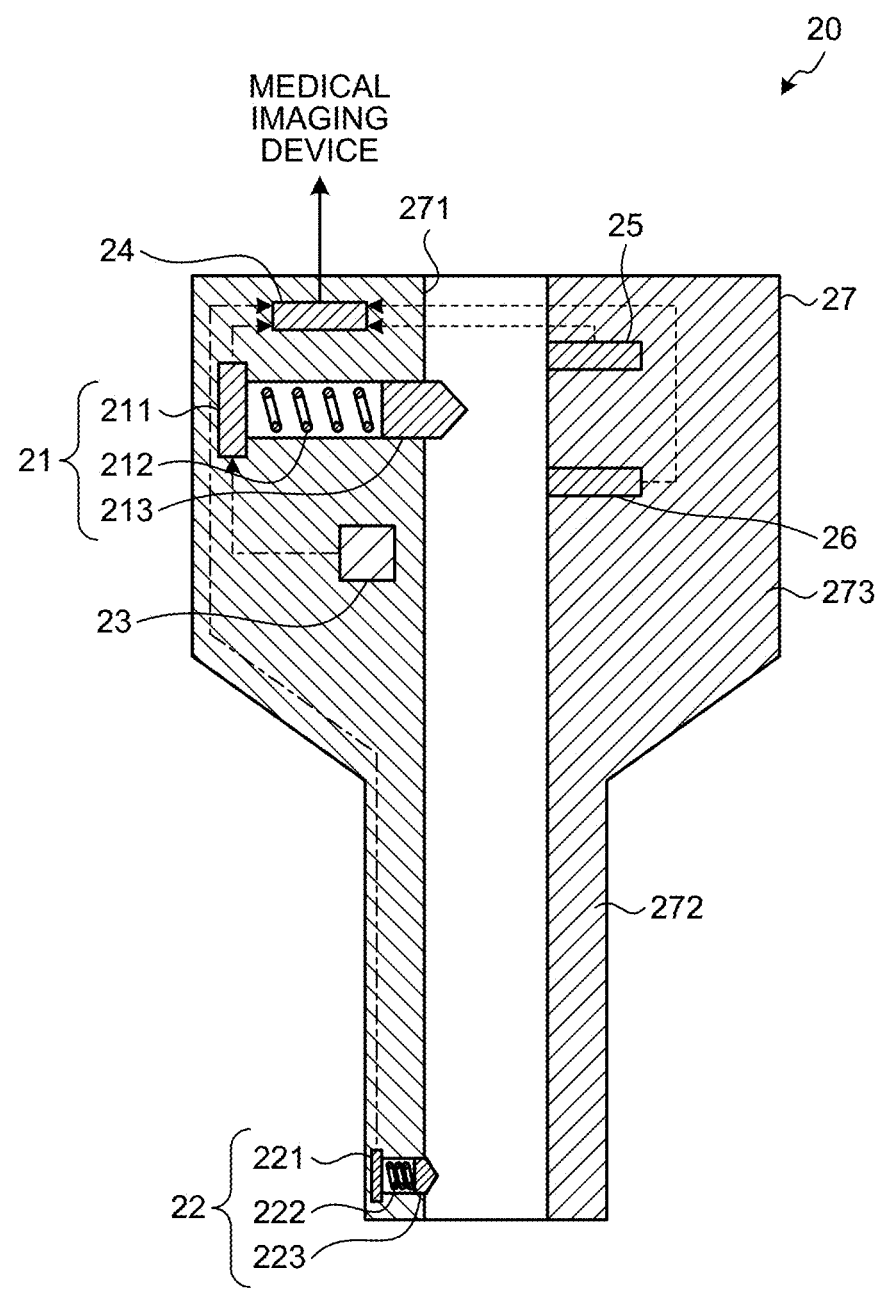
FIG. 3 is a schematic diagram illustrating a section of a trocar according to the first embodiment.

First, the configuration of the trocar 20 will be described. FIG. 3 is a schematic diagram illustrating a section of the trocar 20. The trocar 20 illustrated in FIGS. 2 and 3 includes a first detection unit 21, a second detection unit 22, an acquisition unit 23, a communication unit 24, a third detection unit 25, a fourth detection unit 26, and a main body 27.

The first detection unit 21 is disposed in an insertion direction of an insertion portion 271 (hole) formed on the main body 27 and detects, as a first state, the position of the medical instrument 40 inserted in the insertion portion 271. Specifically, the first detection unit 21 detects, as the first state, that the medical instrument 40 is located inside the trocar 20. The first detection unit 21 includes a pressure sensor 211, a biasing member 212, and a fitting member 213. The pressure sensor 211 detects a biasing state of the biasing member 212. The biasing member 212 biases the fitting member 213 toward the insertion portion 271. The fitting member 213 is projectable to the insertion portion 271 and fitted with a recess 43 formed on the medical instrument 40 (described below).

The second detection unit 22 is disposed in the insertion direction of the insertion portion 271 formed on the main body 27 at such a position that an insertion distance of the medical instrument 40 is longer than an insertion distance of the medical instrument 40 in a case of being detected by the first detection unit 21 and detects, as a second state, the position of the medical instrument 40 inserted in the insertion portion 271. Specifically, the second detection unit 22 detects, as the second state, a state where at least a part of the medical instrument 40 is inserted and exposed into the subject $O_1$ through the trocar 20. The second detection unit 22 includes a pressure sensor 221, a biasing member 222, and a fitting member 223. The pressure sensor 221 detects a biasing state of the biasing member 222. The biasing member 222 biases the fitting member 223 toward the insertion portion 271. The fitting member 223 is projectable to the insertion portion 271 and fitted with a recess 42 formed on the medical instrument 40 (described below).

The acquisition unit 23 acquires medical instrument information about the medical instrument 40 inserted in the insertion portion 271 of the main body 27. Specifically, the acquisition unit 23 acquires, through wireless communication, the medical instrument information from an IC chip 41 which is installed inside the medical instrument 40 (described below) and records thereon the medical instrument information about the medical instrument 40. For example, the acquisition unit 23 acquires the medical instrument information from a radio frequency identifier (RFID) installed inside the medical instrument 40. The acquisition unit 23 is implemented using, for example, an IC chip reader or an RFID reader. Here, the medical instrument information includes at least one of the type of the medical instrument 40 (e.g., forceps or an electric scalpel), the model number of the medical instrument 40, the technique in which the medical instrument 40 is used, the shape of the medical instrument 40, and the date of manufacture of the medical instrument 40. Note that although, in FIGS. 2 and 3, the acquisition unit 23 is mounted on the main body 27 of the trocar 20, the acquisition unit 23 may be, for example, detachably attached to the main body 27 as long as the acquisition unit 23 is capable of acquiring the medical instrument information from the IC chip 41 of the medical instrument 40. For example, the acquisition unit 23 may be a reader capable of reading a two-dimensional code printed on the medical instrument 40.

The communication unit 24 transmits, to the medical imaging device 30 via a transmission cable, each of a detection result of the first detection unit 21, a detection result of the second detection unit 22, an acquisition result of the acquisition unit 23, a detection result of the third detection unit 25, and a detection result of the fourth detection unit 26. The communication unit 24 performs the transmission in accordance with a predetermined communication format. The communication unit 24 is implemented using, for example, a communication module. Note that although, in FIGS. 1 to 3, the communication unit 24 transmits various detection results and acquisition results to the medical imaging device 30 in a wired manner, the communication unit 24 may transmit various detection results and acquisition results to the medical imaging device 30 or the control device 80, for example, through wireless communication. Wi-Fi (registered trademark) or Bluetooth (registered trademark) is used as the wireless communication.

The third detection unit 25 detects an insertion amount of the medical instrument 40 inserted in the insertion portion 271 of the main body 27. Specifically, the third detection unit 25 detects, as the insertion amount, a projecting length of the medical instrument 40 from a distal end of the trocar 20. The third detection unit 25 is implemented using, for example, a displacement sensor, an encoder, or a photoelectric sensor.

The fourth detection unit 26 detects, at every predetermined time, a rotation amount of the medical instrument 40 which rotates about the insertion portion 271 of the main body 27. The fourth detection unit 26 is implemented using, for example, a displacement sensor, an encoder, or a photoelectric sensor.

The main body 27 has a tubular shape and includes the insertion portion 271 into which the medical instrument 40 is insertable from the outside, a projection 272 which is inserted into the subject $O_1$, and an exposed portion 273 which is exposed from the subject $O_1$. The projection 272 of the main body 27 is inserted into the subject $O_1$ through a hole (not illustrated) formed on the subject $O_1$.

Configuration of Medical Imaging Device

Next, the configuration of the medical imaging device 30 will be described. The medical imaging device 30 includes an imaging unit 31, a communication unit 32, and an imaging control unit 33.

The imaging unit 31 generates image data by capturing an image of the observation object inside the subject $O_1$ and outputs the image data to the communication unit 32 under control of the imaging control unit 33. The imaging unit 31 includes an optical system 311 and an image sensor 312. The optical system 311 includes one or more lenses. The optical system 311 condenses reflected light and return light from the observation object to form a subject image on a light receiving surface of the image sensor 312. The image sensor 312 is implemented using, for example, an image sensor such as a charge coupled device (CCD) sensor or a complementary metal oxide semiconductor (COMS) sensor. The image sensor 312 generates image data by performing photoelectric conversion on the subject image formed on the light receiving surface by the optical system 311 and transmits the image data to the communication unit 32 under control of the imaging control unit 33.

The communication unit 32 transmits, to the control device 80, image data input from the imaging unit 31 and detection results and acquisition results input from the trocar 20 under control of the imaging control unit 33. The communication unit 32 performs, for example, P/S conversion processing on the image data and transmits the image data to the control device 80. The communication unit 32 is implemented using, for example, a P/S conversion circuit and a communication module. Note that the communication unit 32 may transmit, for example, image data to the control device 80 through wireless communication or optical communication.

The imaging control unit 33 controls each unit of the medical imaging device 30. The imaging control unit 33 is implemented using, for example, a memory and a processor including hardware such as a CPU or an FPGA.

Configuration of Control Device

Next, the configuration of the control device 80 will be described. The control device 80 includes a first communication unit 81, an image processing unit 82, an input unit 83, an estimation unit 84, a recording unit 85, a second communication unit 86, and a control unit 87.

The first communication unit 81 transmits various pieces of control data to the medical imaging device 30 and outputs, to the image processing unit 82 or the control unit 87, various pieces of data transmitted from the medical imaging device 30 under control of the control unit 87. The first communication unit 81 is implemented using, for example, an S/P conversion circuit and a communication module. Further, the first communication unit 81 may transmit various pieces of data to the medical imaging device 30 through wireless communication or optical communication.

The image processing unit 82 performs various image processing operations on image data input from the medical imaging device 30 via the first communication unit 81 and outputs the image data to the display device 70 to cause the display device 70 to display a live view image based on the image data under control of the control unit 87. Further, the image processing unit 82 generates, based on simulation image data (polygon image data) acquired from the image server 90 (described below) and an estimation result of the estimation unit 84 (described below), a simulation image (a simulation image obtained by turning the polygon image data into graphics) of the observation object inside the subject $O_1$ and outputs the simulation image to the display device 70 to cause the display device 70 to display the simulation image under control of the control unit 87. The image processing unit 82 is implemented using a memory and a processor including hardware such as a graphics processing unit (GPU) and an FPGA.

The input unit 83 receives input of an operation from a user and outputs a signal to the control unit 87 in accordance with details of the received operation. The input unit 83 is implemented using, for example, a mouse, a keyboard, a touch panel, a switch, and a button.

The estimation unit 84 estimates, based on the live view image based on the image data and the simulation image data acquired from the image server 90 via the second communication unit 86, an organ as the observation object of the subject $O_1$ included in the live view image and the position thereof, and outputs a result of the estimation to the image processing unit 82 and the control unit 87 under control of the control unit 87. The estimation unit 84 is implemented using a learned model that machine-learns, through, for example, deep learning, learning parameters (teacher data) such as a live view image, an organ included in the live view image and the position thereof, distance information indicating the distance between the distal end of the medical imaging device 30 and the organ, feature data of the live view image, and a plurality of pieces of simulation image data (e.g., polygon data based on at least one of CT image data and MRI image data), and outputs, as an output parameter, an estimation result obtained by estimating the organ as the observation object of the subject $O_1$ included in the live view image and the position thereof. Here, examples of the machine learning include deep neural network (DNN), convolutional neural network (CNN), and recurrent neural network (RNN). Further, when a live view image based on image data generated by the medical imaging device 30 is multi-spectral image data obtained through the application of multi-spectral light from the light source device 60, the estimation unit 84 estimates, using a difference in reflected light frequency (for each spectrum) included in the multi-spectral image data, a living tissue type (e.g., an organ such as the gallbladder or the pancreas, a blood vessel, a nerve, a lymphatic vessel, the ureter, and fat) of each part as the observation object of the subject $O_1$ included in the multi-spectral image data and the position (area) thereof, and outputs a result of the estimation to the image processing unit 82 and the control unit 87. The estimation unit 84 is implemented using a memory, and a processor including hardware such as a GPU.

The recording unit 85 records various pieces of data relating to the medical observation system 1. The recording unit 85 includes a program recording unit 851 which records various programs executed by the medical observation system 1. The recording unit 85 is implemented using, for example, a random access memory (RAM), a read only memory (ROM), a hard disk drive (HDD), and a solid state drive (SSD).

The second communication unit 86 acquires patient simulation data corresponding to the subject $O_1$ from the image server 90 via the network 100 and outputs the acquired patient simulation image data to the control unit 87 and the image processing unit 82 under control of the control unit 87. The second communication unit 86 is implemented using, for example, a communication module.

The control unit 87 controls each unit of the control device 80. The control unit 87 is implemented using a memory and a processor including hardware such as a CPU. The control unit 87 causes, based on a detection result of at least one trocar 20 into which the medical instrument 40, 50 grasped by the operator is inserted and which is capable of detecting a first state and a second state which indicate an insertion state of the medical instrument 40, 50 into the subject $O_1$, the display device 70 to display at least one of a first image generated by capturing an image of the observation object inside the subject $O_1$ and a second image of the observation object inside the subject $O_1$, the second image being previously acquired. The first image is the live view image. On the other hand, the second image is the simulation image. Specifically, when the medical instrument 40, 50 is in the second state, the control unit 87 causes the display device 70 to display the live view image. On the other hand, when the medical instrument 40, 50 is in the first state, the control unit 87 causes the display device 70 to display at least one of the live view image and the simulation image. Further, the control unit 87 causes the display device 70 to display a medical instrument image corresponding to the medical instrument in a superimposed manner on the simulation image based on medical instrument information about the medical instrument 40, 50 detected by the trocar 20.

Further, the control unit 87 controls a display mode of the medical instrument image and the simulation image based on details of an operation of the operator on the medical instrument 40, 50. Specifically, the control unit 87 causes the display device 70 to display the simulation image with the observation object rotated in at least one of the horizontal direction and the vertical direction based on the insertion amount of the medical instrument 40, 50 into the insertion portion 271 of the trocar 20 and the rotation amount of the medical instrument 40, 50 which rotates about the insertion portion 271 of the trocar 20, the insertion amount and the rotation amount being detected by the trocar 20. Further, when switching from the live view image to the simulation image, the control unit 87 causes the display device 70 to display the simulation image with the position of the organ included in the simulation image aligned with the position of the organ included in the live view image based on the estimation result of the estimation unit 84. Further, when the medical instrument 40, 50 is in the first state, the control unit 87 causes the display device 70 to display the live view image and the simulation image in parallel. Alternatively, the control unit 87 causes the display device 70 to display the live view image reduced in size and superimposed on the simulation image. Furthermore, when switching from the live view image to the simulation image, the control unit 87 causes the display device 70 to output a warning.

Configuration of Image Server

Next, the configuration of the image server 90 will be described. The image server 90 includes a communication unit 91, a patient simulation image data recording unit 92, a patient two-dimensional image data recording unit 93, a patient data recording unit 94, a medical instrument data recording unit 95, a generation unit 96, and a server control unit 97.

The communication unit 91 outputs, to the control device 80, patient simulation image data for the subject $O_1$ requested from the control device 80 via the network 100 under control of the server control unit 97. The communication unit 91 is implemented using, for example, a communication module.

The patient simulation image data recording unit 92 is implemented using, for example, an HDD and an SSD. The patient simulation image data recording unit 92 records a patient ID identifying each of patients and simulation image data in association with each other. Here, the simulation image data is three-dimensional image data constituted of three-dimensional polygon data that is generated by the generation unit 96 (described below) based on two-dimensional image data acquired through, for example, a CT inspection or an MRI inspection on the patient (subject $O_1$). Note that the simulation image data is data for performing a surgery simulation using the organ in a three-dimensional space and includes data relating to the organ or the medical instrument. The simulation image data for each organ or medical instrument includes the following parameters: (1) position (the position of the organ (coordinate information)), and (2) shape (the shape of the organ, the shape of each medical instrument), and is defined by, for example, polygon data in the three-dimensional space. The simulation image data for each organ or medical instrument may further include the following parameters (3) to (7): (3) mass density, (4) stiffness, (5) friction, (6) viscosity, and (7) sense of touch. The simulation image data may further include time-series change information about movement or deformation with time of the medical instrument or the organ.

The patient two-dimensional image data recording unit 93 records the patient ID identifying each of patients and two-dimensional image data acquired through, for example, a CT inspection or an MRI inspection in association with each other. The patient two-dimensional image data recording unit 93 is implemented using, for example, an HDD and an SSD.

The patient data recording unit 94 records the patient ID identifying each of patients and patient chart data (a medical examination result or symptom) of the patient in association with each other. The patient data recording unit 94 is implemented using, for example, an HDD and an SSD.

The medical instrument data recording unit 95 records medical instrument information of each of medical instruments and a medical instrument image (animation image data) of the medical instrument in association with each other. The medical instrument data recording unit 95 is implemented using, for example, an HDD and an SSD.

The generation unit 96 generates simulation image data of a patient based on the two-dimensional image data recorded by the patient two-dimensional image data recording unit 93 under control of the server control unit 97. For example, the generation unit 96 generates three-dimensional simulation image data based on the two-dimensional image data recorded by the patient two-dimensional image data recording unit 93 and records the simulation image data on the patient simulation image data recording unit 92.

The server control unit 97 acquires, from the patient simulation image data recording unit 92, simulation image data corresponding to the subject $O_1$ requested from the control device 80 and input through the communication unit 91, and causes the communication unit 91 to transmit the acquired patient simulation image data. The server control unit 97 is implemented using a memory and a processor including hardware such as a CPU.

Detection State of Medical Instrument Detected by Trocar

Next, a detection state of the inserted medical instrument 40, 50 detected by the trocar 20 will be described. FIGS. 4A to 4E are sectional views schematically illustrating the detection state of the medical instrument 40 inserted into the trocar 20. Note that, in FIGS. 4A to 4E, the subject $O_1$ is omitted to simplify description. Further, in FIGS. 4A to 4E, a case where forceps are inserted as the medical instrument 40 will be described.

Figure 4A:
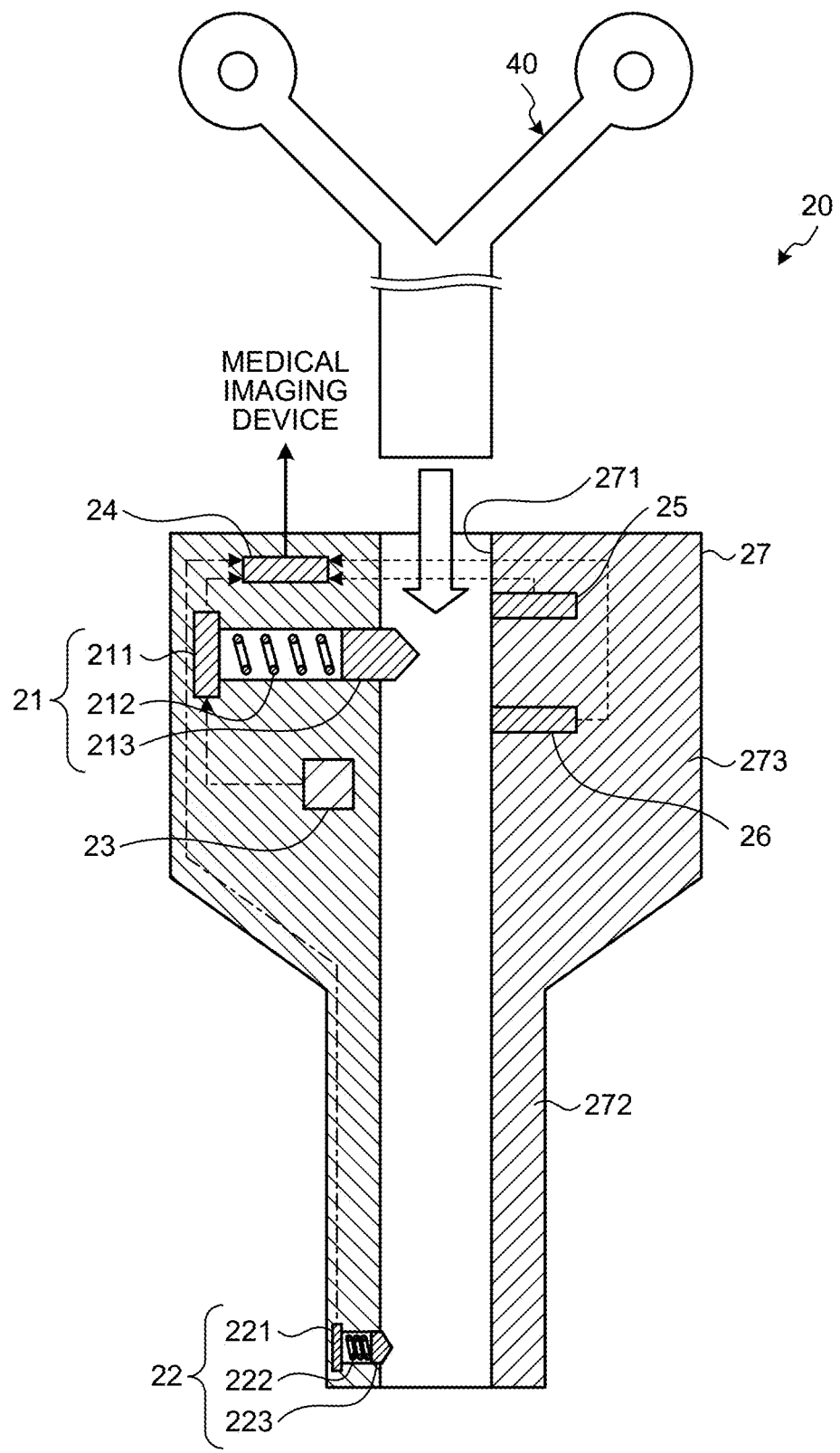
FIG. 4A is a sectional view schematically illustrating a detection state of a medical instrument inserted into the trocar according to the first embodiment.
Figure 4B:
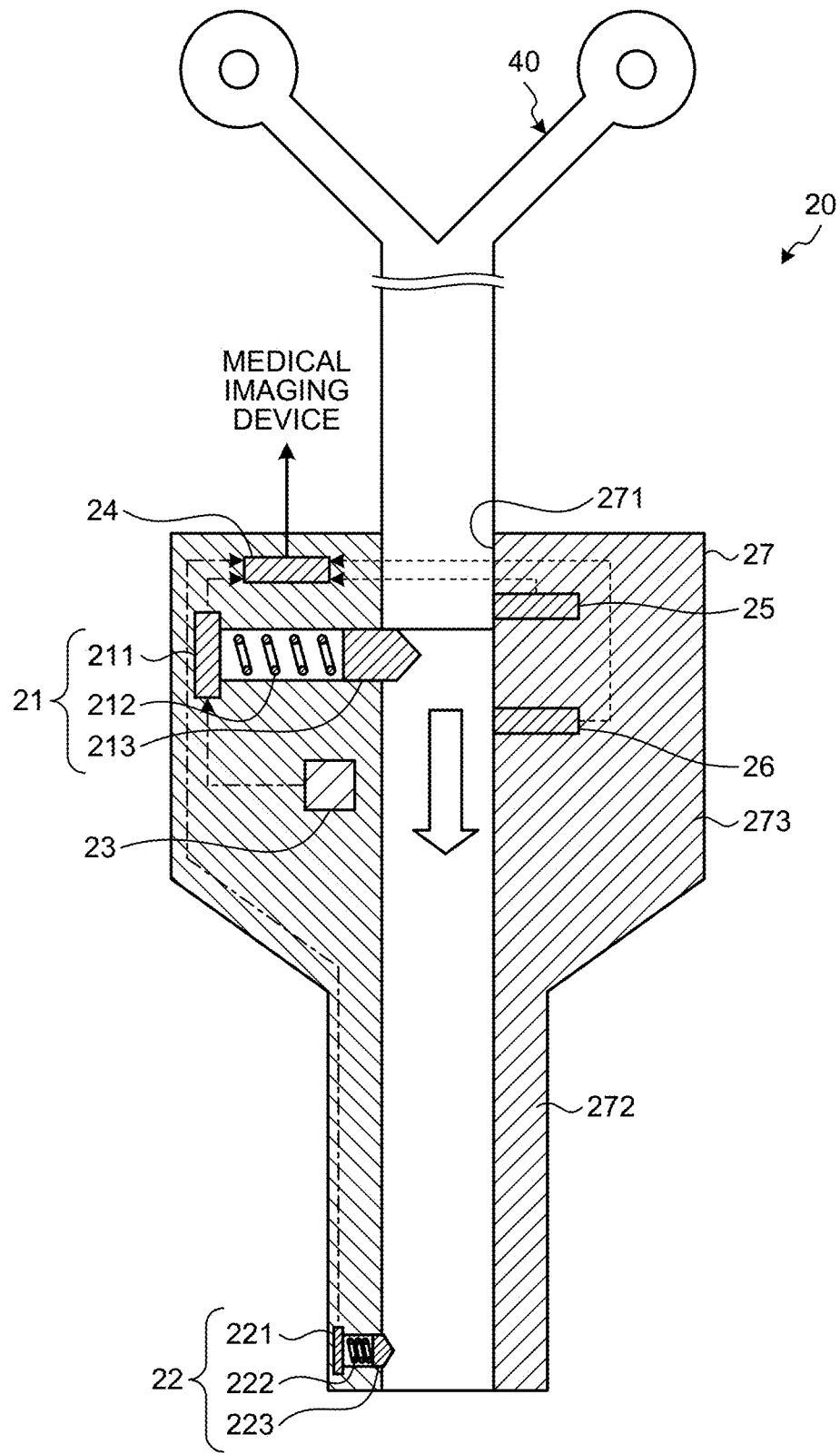
FIG. 4B is a sectional view schematically illustrating a detection state of the medical instrument inserted into the trocar according to the first embodiment.
Figure 4C:
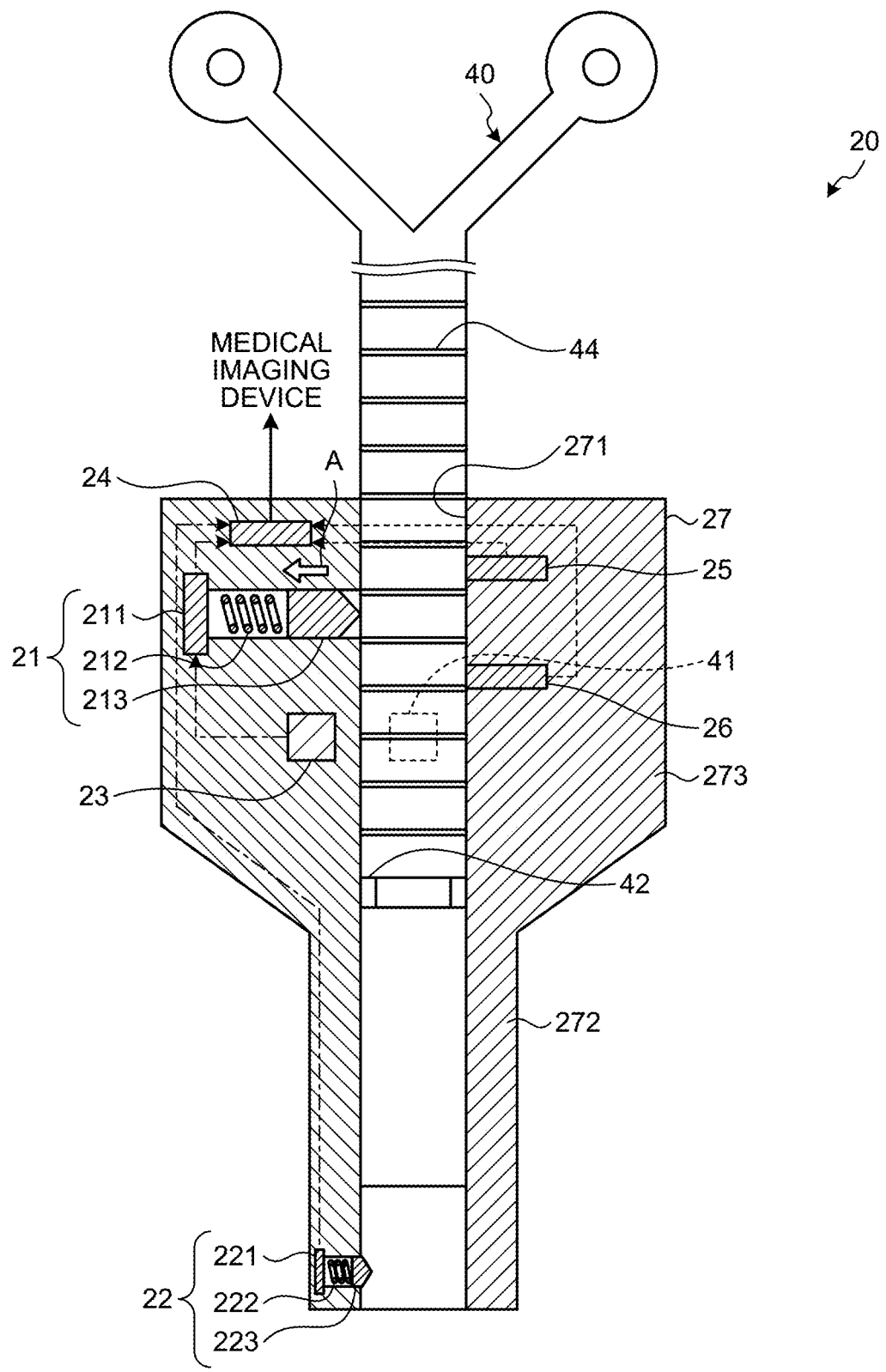
FIG. 4C is a sectional view schematically illustrating a detection state of the medical instrument inserted into the trocar according to the first embodiment.

As illustrated in FIG. 4A, the operator first inserts the medical instrument 40 into the insertion portion 271 of the trocar 20 inserted inside the subject $O_1$. In this case, as illustrated in FIG. 4B, as the operator inserts the medical instrument 40, the distal end of the medical instrument 40 comes into contact with the fitting member 213 of the first detection unit 21. At this time, as illustrated in FIG. 4C, the operator further pushes the medical instrument 40 in the insertion direction of the trocar 20, which makes the pressing force applied to the medical instrument 40 by the operator larger than the biasing force of the biasing member 212. As a result, the fitting member 213 is retracted to the outer edge side of the insertion portion 271 (refer to arrow A). This enables the operator to insert the medical instrument 40 in the insertion direction. In this case, the first detection unit 21 outputs a detection result indicating that the medical instrument 40 has become the first state to the control device 80 via the medical imaging device 30. Further, as illustrated in FIG. 4C, the acquisition unit 23 acquires medical instrument information from the IC chip 41 installed in the medical instrument 40 and outputs the medical instrument information to the control device 80 via the medical imaging device 30. In the first state of the medical instrument 40, the control unit 87 causes the display device 70 to display the second image of the observation object inside the subject $O_1$, the second image being previously acquired (simulation mode). Further, as illustrated in FIG. 4C, the third detection unit 25 outputs, to the control device 80 via the medical imaging device 30, the detected insertion amount of the medical instrument 40 inserted into the insertion portion 271 of the trocar 20 by the operator. Furthermore, as illustrated in FIG. 4C, the fourth detection unit 26 outputs, to the control device 80 via the medical imaging device 30, the detected rotation amount of the medical instrument 40 rotated inside the insertion portion 271 of the trocar 20 by the operator.

Figure 4D:
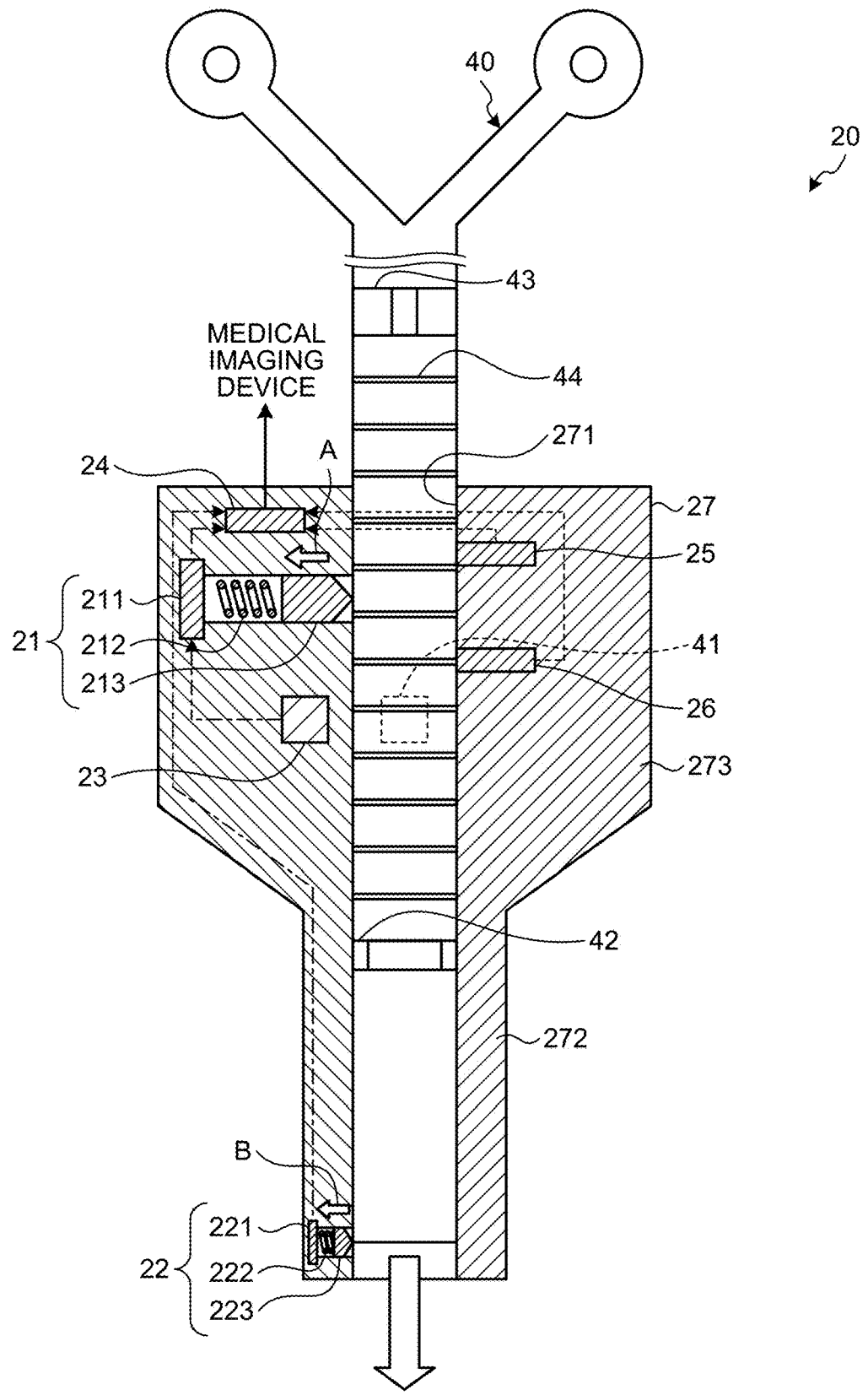
FIG. 4D is a sectional view schematically illustrating a detection state of the medical instrument inserted into the trocar according to the first embodiment.

Then, as illustrated in FIG. 4D, in a state where the first detection unit 21 has detected the first state, the operator further inserts the medical instrument 40 in the insertion direction. As a result, the distal end of the medical instrument 40 comes into contact with the fitting member 223 of the second detection unit 22. In this case, as illustrated in FIG. 4D, the operator further pushes the medical instrument 40 in the insertion direction of the trocar 20 as with the case of the first detection unit 21, which makes the pressing force applied to the medical instrument 40 by the operator larger than the biasing force of the biasing member 222. As a result, the fitting member 223 is retracted to the outer edge side of the insertion portion 271 (refer to arrow B). This enables the operator to insert the medical instrument 40 into the subject $O_1$. In this case, the second detection unit 22 outputs a detection result indicating that the medical instrument 40 has become the second state to the control device 80 via the medical imaging device 30.

Then, as illustrated in FIG. 4E, the fitting member 213 of the first detection unit 21 and the fitting member 223 of the second detection unit 22 are respectively fitted with the recess 42 having an annular shape and the recess 43 having an annular shape on the medical instrument 40. In this case, when the distal end of the medical instrument 40 passes the fitting member 223 of the second detection unit 22, the control unit 87 causes the display device 70 to display a live view image generated by capturing an image of the observation object inside the subject $O_1$ from the previously-acquired simulation image of the observation object inside the subject $O_1$ (switches from the simulation mode to the live view mode). Accordingly, it is possible to prevent the medical instrument 40 from coming out of the trocar 20 against the operator's will. Further, the operator may smoothly switch from the simulation image to the live view image. Furthermore, even when the fitting member 213 of the first detection unit 21 and the fitting member 223 of the second detection unit 22 are in a fitted state, the operator may use the medical instrument 40 while rotating the medical instrument 40 due to the annular shape of the recess 42 and the recess 43. In this case, the control unit 87 causes the display device 70 to display the simulation image with the observation object rotated in at least one of the horizontal direction and the vertical direction based on the insertion amount of the medical instrument 40 detected by the third detection unit 25 and the rotation amount of the medical instrument 40 detected by the fourth detection unit 26. This enables the operator to virtually check the observation object included in the simulation image in another view point by operating the medical instrument 40.

Then, the operator performs procedures on the observation object of the subject $O_1$ while watching the live view image displayed by the display device 70. In this case, when a mark may not be found for the observation object (procedure target) included in the live view image displayed by the display device 70 or when the current state differs from a state estimated in the CT image or the MRI image checked before the surgery, the operator performs an operation of pulling the medical instrument 40 so that the medical instrument 40 becomes the first state where the medical instrument 40 is not exposed into the subject $O_1$. Accordingly, the medical observation system 1 switches from the live view mode in which the live view image is displayed to the simulation mode in which the simulation image of the subject $O_1$ is displayed and the procedures may be virtually performed on the observation object. As a result, the operator may instantaneously switch between the live view mode and the simulation mode while grasping the medical instrument 40. Further, when the medical observation system 1 is switched to the simulation mode, the fitting member 223 of the second detection unit 22 projects in the direction perpendicular to the insertion direction of the insertion portion 271, which makes it possible to prevent the medical instrument 40 from being inserted into the subject $O_1$ against the operator's will. At this time, the control unit 87 causes the display device 70 to display the simulation image with the observation object rotated in at least one of the horizontal direction and the vertical direction based on the insertion amount of the medical instrument 40 detected by the third detection unit 25 and the rotation amount of the medical instrument 40 detected by the fourth detection unit 26. This enables the operator to virtually check the observation object included in the simulation image in another view point by operating the medical instrument 40 even when the current state differs from the state estimated in the CT image or the MRI image checked before the surgery.

Process of Medical Observation System

Figure 5:
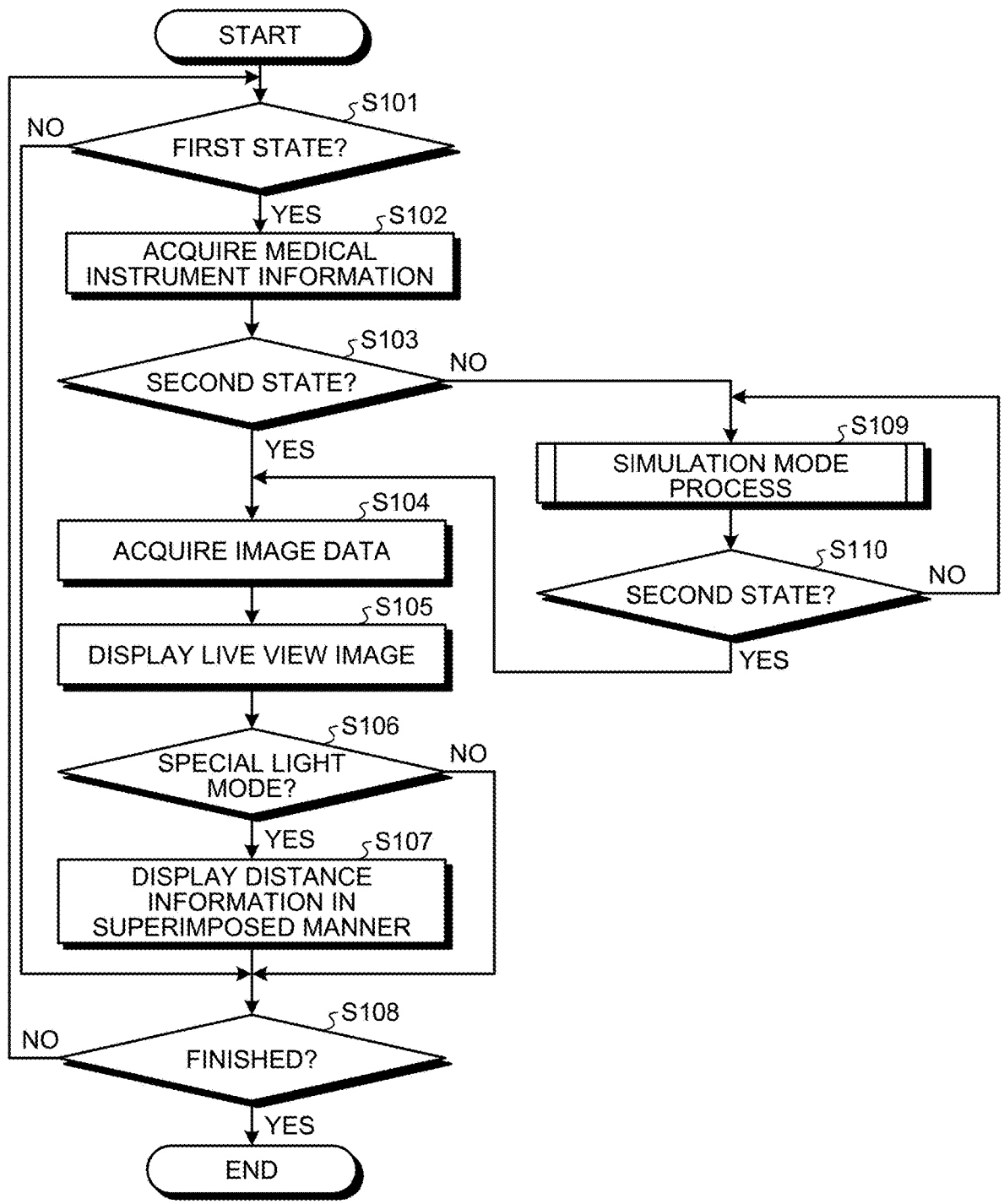
FIG. 5 is a flowchart illustrating an outline of a process executed by the medical observation system according to the first embodiment.

Next, a process executed by the medical observation system 1 will be described. FIG. 5 is a flowchart illustrating an outline of the process execute by the medical observation system 1.

As illustrated in FIG. 5, the control unit 87 first determines whether the medical instrument 40 is in the first state based on a detection result detected by the first detection unit 21 of the trocar 20 (Step S101). Specifically, the control unit 87 determines whether a detection result indicating that the insertion of the medical instrument 40 has been detected has been input from the first detection unit 21 of the trocar 20. When the control unit 87 determines that the medical instrument 40 is in the first state (Step S101: Yes), the medical observation system 1 shifts to Step S102 (described below). On the other hand, when the control unit 87 determines that the medical instrument 40 is not in the first state (Step S101: No), the medical observation system 1 shifts to Step S108 (described below).

In Step S102, the control unit 87 acquires medical instrument information about the medical instrument 40 acquired by the acquisition unit 23. Specifically, the acquisition unit 23 acquires medical instrument information from the IC chip 41 of the medical instrument 40 and outputs the acquired medical instrument information to the control unit 87 via the medical imaging device 30.

Then, the control unit 87 determines whether the medical instrument 40 is in the second state based on a detection result detected by the second detection unit 22 of the trocar 20 (Step S103). Specifically, the control unit 87 determines whether a detection result indicating that the insertion of the medical instrument 40 has been detected (live view mode) has been input from the second detection unit 22 of the trocar 20. When the control unit 87 determines that the medical instrument 40 is in the second state (Step S103: Yes), the medical observation system 1 shifts to step S104 (described below) (transitions to the live view mode). On the other hand, when the control unit 87 determines that the medical instrument 40 is not in the second state (Step S103: No), the medical observation system 1 shifts to step S109 (described below) (transitions to the simulation mode).

In step S104, the control unit 87 acquires, via the first communication unit 81, image data generated by the medical imaging device 30. In this case, the control unit 87 causes the first communication unit 81 to output the image data to the image processing unit 82.

Figure 6:
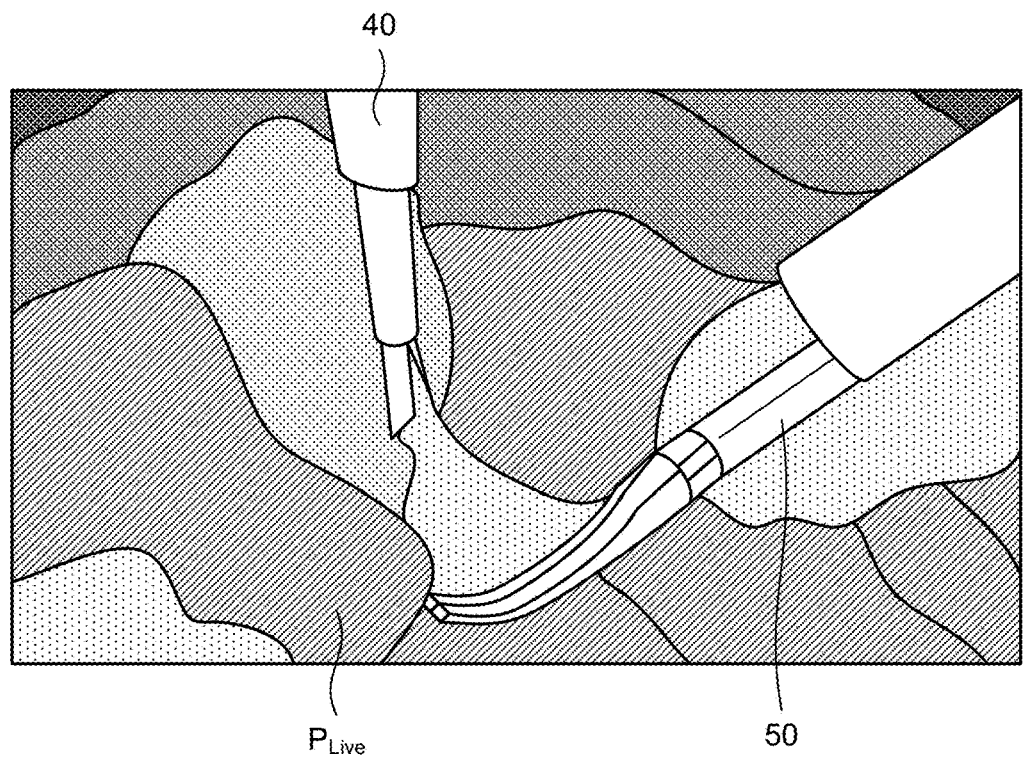
FIG. 6 is a diagram illustrating an example of a live view image displayed by a display device according to the first embodiment.

Then, the control unit 87 causes the image processing unit 82 to perform image processing on the image data acquired by the first communication unit 81 and output the image data to the display device 70 to cause the display device 70 to display a live view image (Step S105). Specifically, as illustrated in FIG. 6, the control unit 87 causes the image processing unit 82 to perform image processing on the image data acquired by the first communication unit 81 and output the image data to the display device 70 to cause the display device 70 to display a live view image $P_{Live}$ based on the image data. This enables the operator to perform procedures on the observation object of the subject $O_1$ while watching the live view image $P_{Live}$ displayed by the display device 70.

Then, the control unit 87 determines whether an instruction signal instructing a special light mode for performing fluorescence observation has been input from the input unit 83 (Step S106). When the control unit 87 determines that the instruction signal instructing the special light mode for performing fluorescence observation has been input from the input unit 83 (Step S106: Yes), the medical observation system 1 shifts to Step S107 (described below). On the other hand, when the control unit 87 determines that the instruction signal instructing the special light mode for performing fluorescence observation has not been input from the input unit 83 (Step S106: No), the medical observation system 1 shifts to Step S108 (described below).

Figure 7:
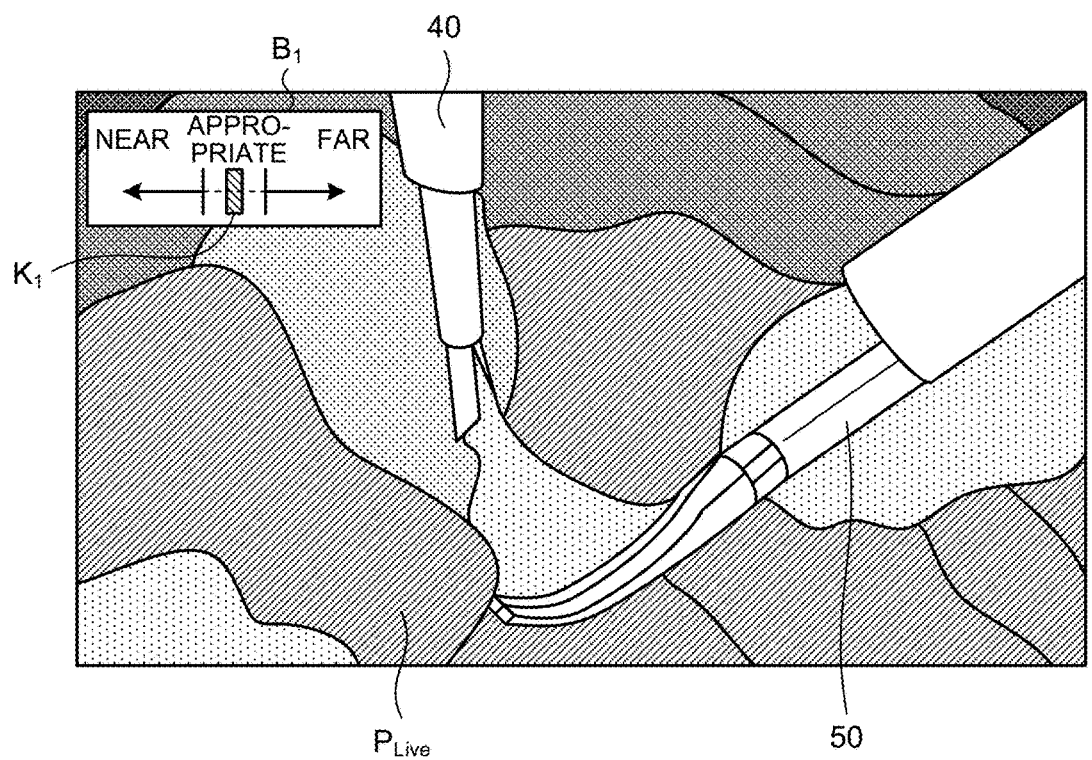
FIG. 7 is a diagram illustrating another example of the live view image displayed by the display device according to the first embodiment.

In step S107, the control unit 87 causes the display device 70 to display, in a superimposed manner on the live view image displayed by the display device 70, distance information including an optimum distance between the observation object and the distal end of the medical imaging device 30 which captures an image of the observation object of the subject $O_1$ in observation of fluorescence of the observation object of the subject $O_1$ based on the distance between the distal end of the medical imaging device 30 and the observation object of the subject $O_1$. Specifically, as illustrated in FIG. 7, the control unit 87 causes the display device 70 to display distance information $B_1$ in a superimposed manner on the live view image $P_{Live}$. The distance information $B_1$ includes a current distance $K_1$ between the observation object of the subject $O_1$ and the distal end of the medical imaging device 30 in observation of fluorescence of the observation object and an optimum distance range $H_1$. Here, the optimum distance range $H_1$ is a distance range between a position where the distal end of the medical imaging device 30 is brought into contact with the observation object and a position where the medical imaging device 30 is pulled toward the trocar 20, that is, toward the near side (operator's side) by 4 cm to 5 cm. This enables the operator to reliably prevent false positive or false negative by observing the current distance $K_1$ included in the distance information $B_1$ and a fluorescence emission amount from the observation object even with the emission amount of fluorescence that looks different depending on the distance between the observation object and the distal end of the medical imaging device 30.

Then, the control unit 87 determines whether an instruction signal for finishing the procedures on the subject O1 has been input from the input unit 83 (Step S108). When the control unit 87 determines that the instruction signal for finishing the procedures on the subject O1 has been input from the input unit 83 (Step S108: Yes), the medical observation system 1 finishes the present process. On the other hand, when the control unit 87 determines that the instruction signal for finishing the procedures on the subject $O_1$ has not been input from the input unit 83 (Step S108: No), the medical observation system 1 returns to step S101 described above.

In step S109, the medical observation system 1 executes a simulation mode process for displaying the simulation image corresponding to the subject $O_1$.

Simulation Mode Process

Figure 8:
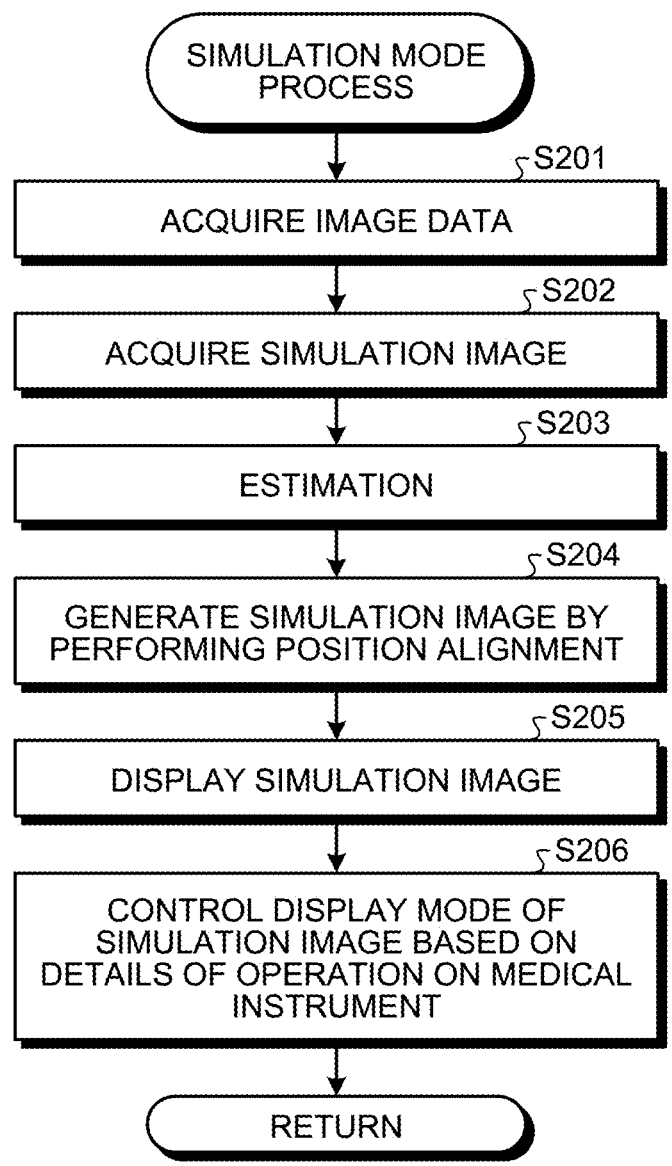
FIG. 8 is a flowchart illustrating an outline of a simulation mode process of FIG. 5.

FIG. 8 is a flowchart illustrating an outline of the simulation mode process in Step S109.

As illustrated in FIG. 8, the control unit 87 acquires, via the first communication unit 81, image data generated by the medical imaging device 30 (Step S201). In this case, the control unit 87 causes the first communication unit 81 to output the image data to the image processing unit 82 and the estimation unit 84.

Then, the control unit 87 acquires simulation image data corresponding to the subject $O_1$ from the image server 90 via the second communication unit 86 and the network 100 (Step S202). Specifically, the control unit 87 acquires, based on a patient ID relating to the subject $O_1$, the patient ID being previously set by a user such as the operator or a nurse, the simulation image data that corresponds to the patient ID of the subject $O_1$ and is generated using two-dimensional image data previously captured for the subject $O_1$ through, for example, a CT inspection or an MRI inspection from the image server 90. In this case, the control unit 87 causes the second communication unit 86 to output the simulation image data to each of the image processing unit 82 and the estimation unit 84.

Then, the estimation unit 84 estimates an organ and a blood vessel which are included in the live view image $P_{Live}$ based on the image data and the position thereof based on the image data generated by the medical imaging device 30 and input from the first communication unit 81 and the simulation image data input from the second communication unit 86 (Step S203). Note that when the image data includes distance information, the estimation unit 84 further uses the distance information in the estimation. In this case, the estimation unit 84 may estimate, using the distance information, the orientation (direction) and the crushed degree of an organ, a blood vessel, and a nerve which are included in the live view image $P_{Live}$ relative to an optical axis of the optical system 311 of the medical imaging device 30 (the insertion direction of the trocar 10). The estimation unit 84 outputs a result of the estimation to the control unit 87 and the image processing unit 82. Further, when the image data generated by the medical imaging device 30 is multi-spectral image data obtained through the application of multi-spectral light from the light source device 60, the estimation unit 84 may cause the display device 70 to display, in a superimposed manner on the position of the live view image, the living tissue type (e.g., an organ such as the gallbladder or the pancreas, a blood vessel, a nerve, a lymphatic vessel, the ureter, and fat) of each part and the position (area) thereof, the living tissue type and the position thereof being estimated by the estimation unit 84 using the difference in reflected light frequency (for each spectrum) included in the multi-spectral image data.

Then, the control unit 87 causes the image processing unit 82 to generate a simulation image by performing position alignment between the live view image $P_{Live}$ based on the estimation result of the estimation unit 84 and the simulation image based on the simulation image data (Step S204). Specifically, the control unit 87 first causes the image processing unit 82 to perform position alignment between the live view image $P_{Live}$ and the simulation image (polygon data) based on the estimation result of the estimation unit 84. Then, the control unit 87 generates a simulation image by turning the simulation image (polygon data) into graphics. Further, the control unit 87 superimposes a medical instrument image virtually representing the medical instrument 40 corresponding to the medical instrument information acquired by the acquisition unit 23 within the simulation image. Furthermore, the control unit 87 causes the image processing unit 82 to superimpose the live view image on the simulation image. Note that the image processing unit 82 may generate the simulation image including the orientation and the crushed degree of the organ in the estimation result of the estimation unit 84.

Figure 9:
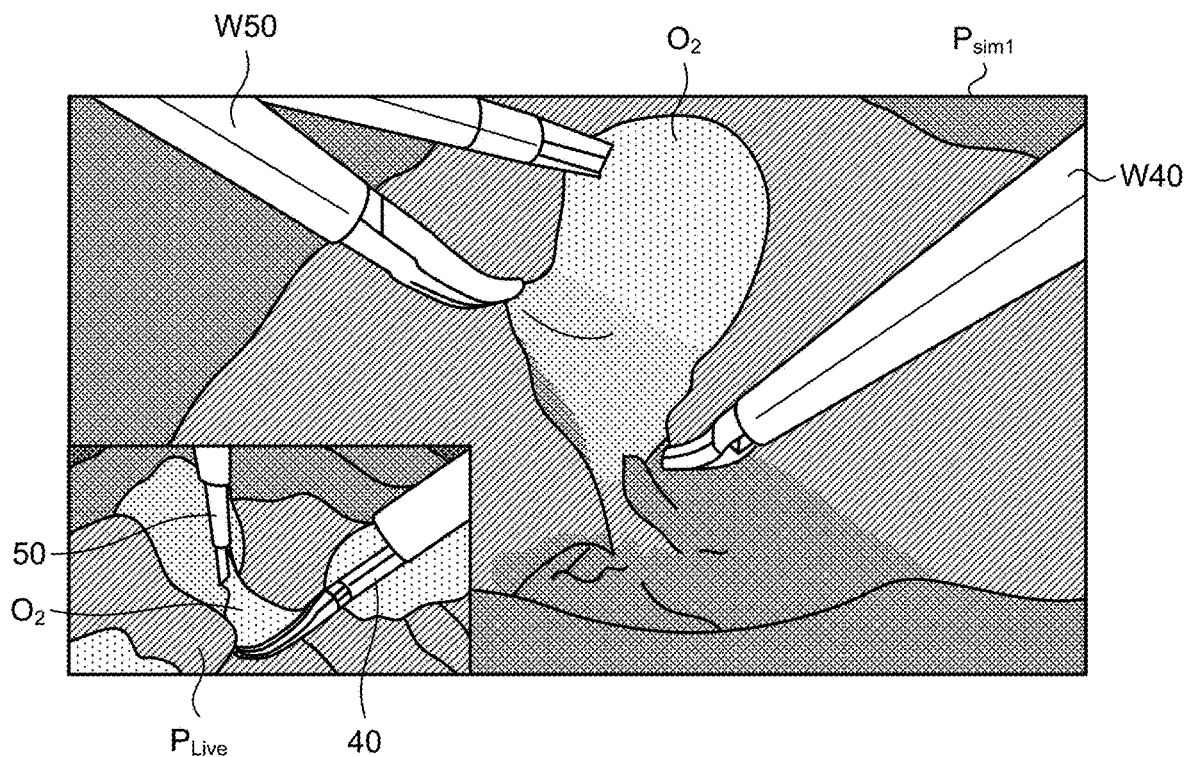
FIG. 9 is a diagram illustrating an example of a simulation image displayed by the display device according to the first embodiment.

FIG. 9 is a diagram illustrating an example of the simulation image displayed by the display device 70. As illustrated in FIG. 9, the control unit 87 causes the image processing unit 82 to superimpose the live view image $P_{Live}$ on the simulation image $P_{sim1}$ and causes the display device 70 to display, in a superimposed manner on the simulation image $P_{sim1}$, the medical instrument images W40, W50 virtually representing the medical instruments 40, 50 corresponding to the medical instrument information acquired by the acquisition unit 23. Note that although, in FIG. 9, the control unit 87 causes the image processing unit 82 to superimpose the live view image $P_{Live}$ on the simulation image $P_{sim1}$, the present disclosure is not limited thereto. The simulation image $P_{sim1}$ and the live view image $P_{Live}$ may be displayed in parallel, or the simulation image $P_{sim1}$ and the live view image $P_{Live}$ may be displayed in parallel with a display area of either the simulation image $P_{sim1}$ or the live view image $P_{Live}$ reduced. Furthermore, the control unit 87 may display text based on text data input by an attending doctor using, for example, a keyboard, a tumor position, and the position of a mark in a superimposed manner on the simulation image $P_{sim1}$.

Figure 10:
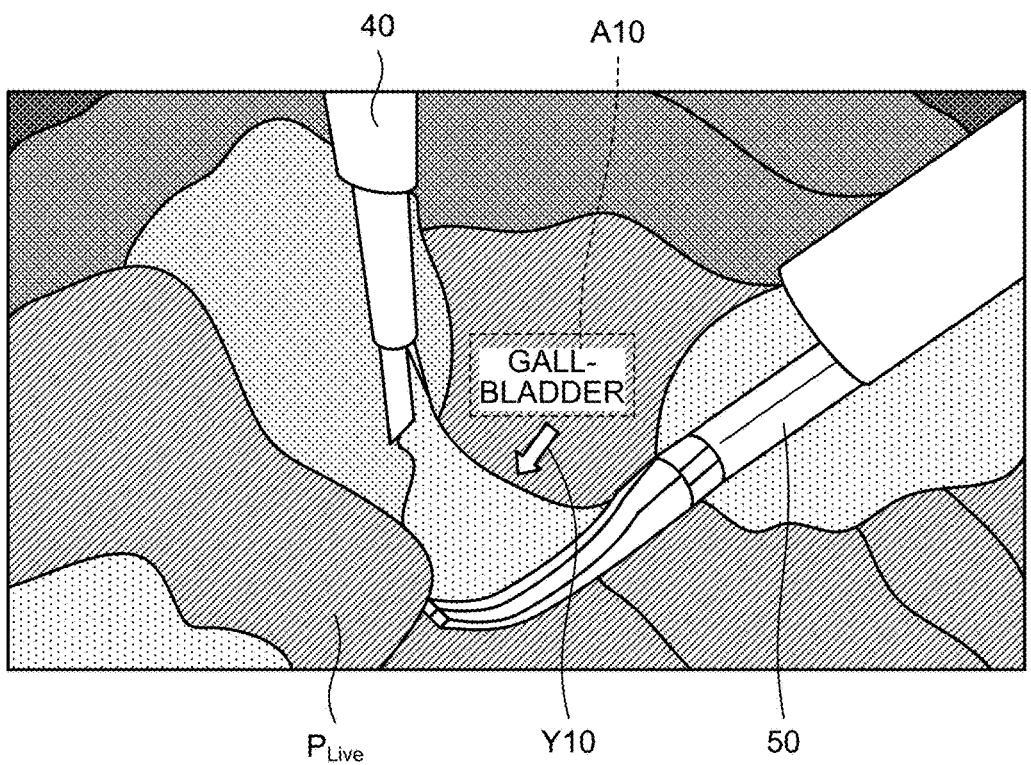
FIG. 10 is a diagram illustrating an example of medical information displayed by the display device according to the first embodiment.

FIG. 10 is a diagram illustrating an example of the medical information displayed by the display device 70. As illustrated in FIG. 10, the control unit 87 may cause the display device 70 to display, as the second image, the medical information in a superimposed manner on the live view image $P_{Live}$. Specifically, as illustrated in FIG. 10, the control unit 87 causes the image processing unit 82 to superimpose, as the medical information, text data A10 indicating being the gallbladder and arrow Y10 indicating the position of the gallbladder on the live view image $P_{Live}$ near the gallbladder included in the live view image $P_{Live}$ and causes the display device 70 to display the superimposed image. Here, examples of the medical information include a blood vessel name, a nerve name, and an organ name. It is needless to say that although the control unit 87 superimposes the medical information near the gallbladder included in the live view image $P_{Live}$, the position of the medical information may be appropriately changed. Further, the control unit 87 may cause the image processing unit 82 to superimpose the live view image $P_{Live}$ on the simulation image $P_{sim1}$ and cause the display device 70 to display the medical information in a superimposed manner on at least one of the simulation image $P_{sim1}$ and the live view image $P_{Live}$. Furthermore, when the image data generated by the medical imaging device 30 is multi-spectral image data generated through the application of multi-spectral light from the multi-spectral light source of the light source device 60, the control unit 87 may cause the display device 70 to display, in a superimposed manner on the position on the live view image, the living tissue type (e.g., an organ such as the gallbladder or the pancreas, a blood vessel, a nerve, a lymphatic vessel, the ureter, and fat) of each part and the position (area) thereof, the living tissue type and the position thereof being estimated by the estimation unit 84 using the difference in reflected light frequency (for each spectrum) included in the multi-spectral image data.

Then, the control unit 87 causes the image processing unit 82 to output the generated simulation image data to the display device 70 to cause the display device 70 to display the simulation image (Step S205). This enables the operator to freely switch between the simulation image $P_{sim1}$ and the live view image $P_{Live}$ without moving the hand off the medical instrument 40. Further, the operator may perform observation without feeling a sense of incongruity because switching is performed from the live view image $P_{Live}$ in a visual field that is the same as the real visual field to the simulation image $P_{sim1}$ in the same visual field. Note that when the control unit 87 causes the display device 70 to display the simulation image $P_{sim1}$, the control unit 87 may cause the display device 70 to issue a warning indicating that the image displayed by the display device 70 is the simulation image $P_{sim1}$ with, for example, sound or text or issue a warning by highlight-displaying an image frame (e.g., flashing the image frame).

Figure 11:
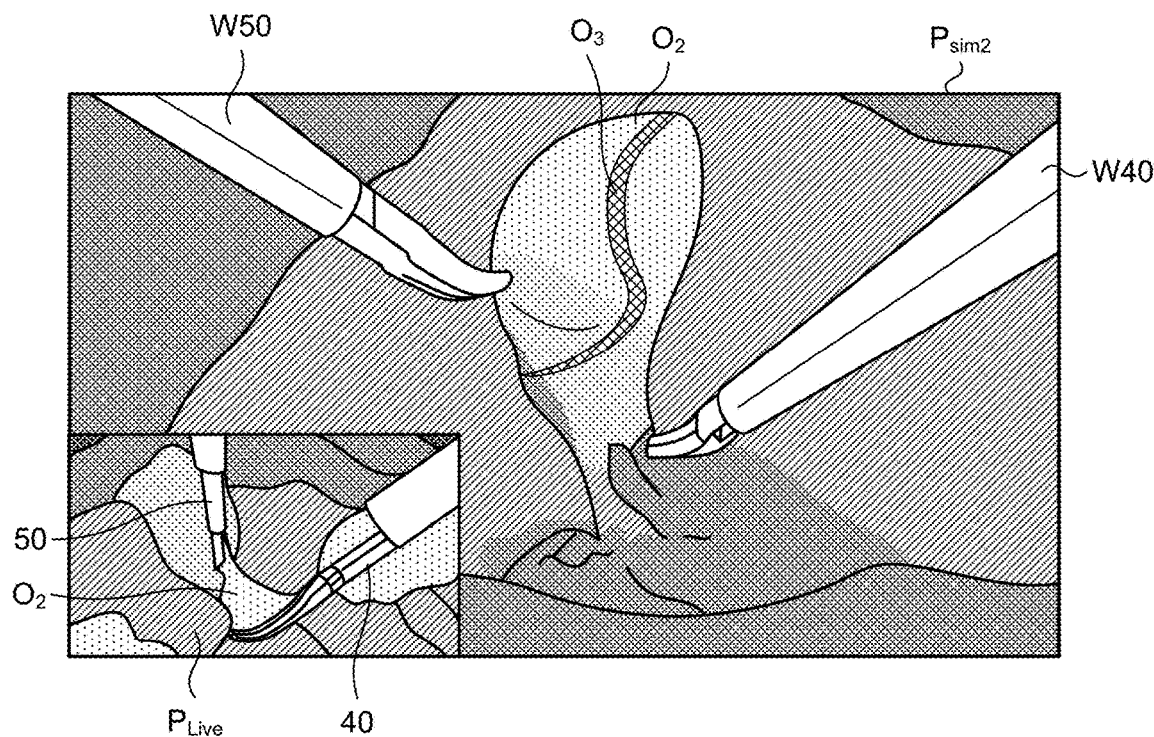
FIG. 11 is a diagram illustrating another example of the simulation image displayed by the display device according to the first embodiment.

Then, the control unit 87 controls the display mode of the simulation image based on details of an operation on the medical instrument 40 (Step S206). Specifically, when, based on the detection result of the third detection unit 25, the operation on the medical instrument 40 is an operation of advancing in the depth direction of an organ $O_2$ on the simulation image $P_{sim1}$, for example, an operation of pushing the medical instrument 40 into the trocar 20 in the insertion direction, the control unit 87 causes the image processing unit 82 to generate a simulation image $P_{sim2}$ processed to include the organ $O_2$ viewed from a next layer of the organ $O_2$ on the current simulation image $P_{sim1}$ (e.g., the layer obtained by slicing the organ into cross sections) or viewed from the back of the organ $O_2$ as illustrated in FIG. 11 and output the generated simulation image $P_{sim2}$ to the display device 70. In this case, the control unit 87 causes, based on the detection result of the third detection unit 25, the image processing unit 82 to generate the simulation image $P_{sim2}$ with the organ $O_2$ rotated in the horizontal direction according to the insertion amount (operation amount) by which the operator pushes the medical instrument 40 into the trocar 20 in the insertion direction and output the generated simulation image $P_{sim2}$ to the display device 70. For example, the control unit 87 determines that the operator pushes the medical instrument 40 into the trocar 20 in the insertion direction based on the detection result of the third detection unit 25, and causes the image processing unit 82 to generate the simulation image $P_{sim2}$ processed into a state viewed from the next layer or the back of the organ $O_2$ on the current simulation image $P_{sim1}$ and output the generated simulation image $P_{sim2}$ to the display device 70. In the case illustrated in FIG. 11, the organ $O_2$ on the simulation image $P_{sim2}$ includes a blood vessel $O_3$ viewed from the back. This enables the operator to virtually observe the organ in a desired view point with an intuitive operation.

Further, the control unit 87 causes the image processing unit 82 to generate the simulation image processed into the state viewed from the next layer (e.g., the layer obtained by slicing the organ into cross sections) or the back of the organ $O_2$ on the current simulation image $P_{sim1}$ according to the operation amount of the operator and output the generated simulation image to the display device 70. Note that the control unit 87 may detect the insertion amount by determining whether a change rate of a pressure value detected by the pressure sensor 211 is equal to or higher than a predetermined value, the pressure value being changed by the fitting member 213 of the first detection unit 21 coming into contact with each of projections 44 which are disposed, in a projecting manner, at predetermined intervals on the outer peripheral side of the medical instrument 40 between the recess 42 and the recess 43 and climbing over the projection 44 at each time. In this case, the control unit 87 may determine an insertion amount (operation amount) by which the operator pushes the medical instrument 40 into the trocar 20 in the insertion direction or an insertion amount (operation amount) by which the operator pulls the medical instrument 40 out according to whether the change rate of the pressure value detected by the pressure sensor 211 is equal to or higher than the predetermined value, the pressure value being changed by the fitting member 213 of the first detection unit 21 climbing over the projection 44. Note that although the control unit 87 determines whether the change rate of the pressure value is equal to or higher than the predetermined value, the control unit 87 may perform determination using, not limited to the change rate, a maximum value and a minimum value of the pressure value. It is needless to say that the shape of the projections 44 on the medical instrument 40 may be appropriately changed or the shape of the projections 44 may be changed according to a predicted pressure value.

Further, the control unit 87 may cause, based on the detection result of the fourth detection unit 26, the image processing unit 82 to generate a simulation image with the organ $O_2$ rotated in the vertical direction according to the rotation amount by which the operator rotates the medical instrument 40 relative to the trocar 20 and output the generated simulation image to the display device 70. It is needless to say that the control unit 87 may cause, based on the detection result of the third detection unit 25 and the detection result of the fourth detection unit 26, the image processing unit 82 to generate a simulation image with the organ $O_2$ rotated in the horizontal direction and the vertical direction and output the generated simulation image to the display device 70.

Figure 12:
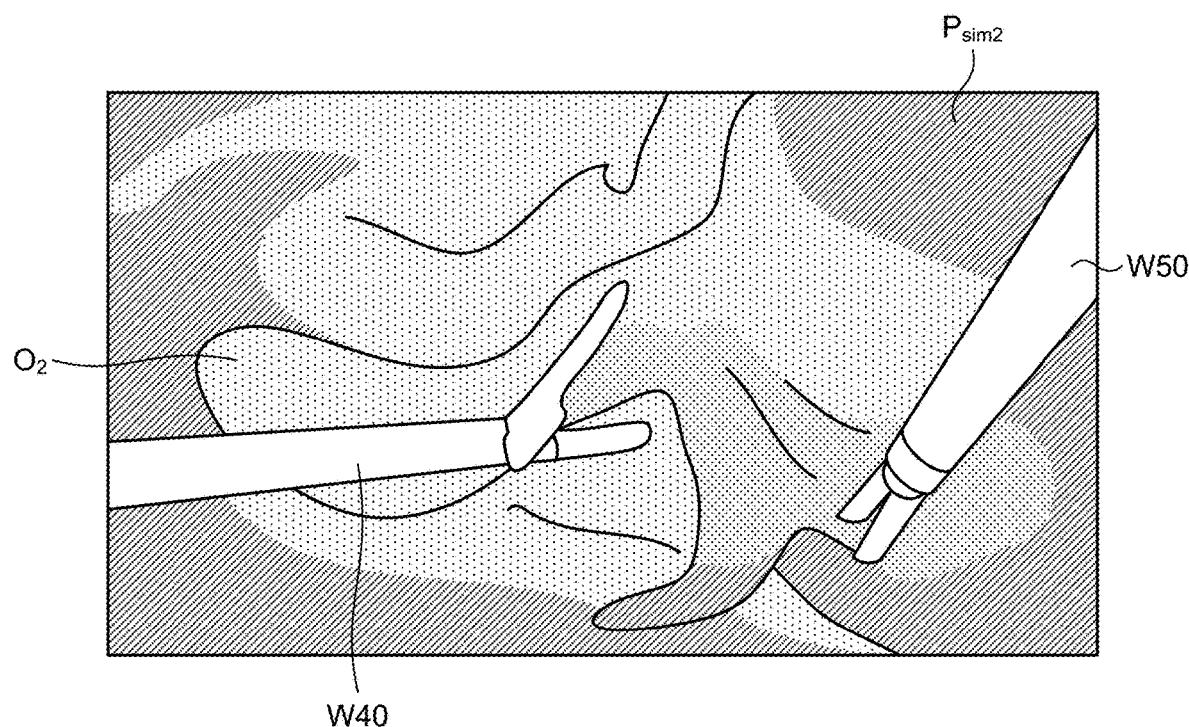
FIG. 12 is a diagram illustrating an example of the simulation image displayed by the display device according to the first embodiment.

Further, when the operation on the medical instrument 40 is an operation of removing fat from the organ $O_2$ on the simulation image $P_{sim2}$ with the medical instrument 40, as illustrated in FIG. 12, the control unit 87 causes the image processing unit 82 to generate the simulation image $P_{sim2}$ for removing fat from the organ $O_2$ with the medical instrument 40 and output the generated simulation image $P_{sim2}$ to the display device 70. This enables the operator to virtually perform simulation on the simulation image $P_{sim2}$. Further, the operator may perform the simulation with the medical instrument 40 the operator is accustomed to using. After Step S206, the process returns to the main routine of FIG. 5 and shifts to Step S110.

Returning back to FIG. 5, description of Steps of Step S110 and thereafter will be continued.

In Step S110, the control unit 87 determines whether the medical instrument 40 is in the second state based on a detection result detected by the second detection unit 22 of the trocar 20. Specifically, the control unit 87 determines whether a detection result indicating that the insertion of the medical instrument 40 has been detected (live view mode) has been input from the second detection unit 22 of the trocar 20. When the control unit 87 determines that the medical instrument 40 is in the second state (Step S110: Yes), the medical observation system 1 shifts to step S104 (transitions to the live view mode). This enables the operator to freely switch, without moving the hand off the medical instrument 40, from the simulation image $P_{sim1}$ to the live view image $P_{Live}$ in the current visual field without feeling a sense of incongruity and perform procedures. Further, the operator may switch between the simulation image $P_{sim1}$ (simulation mode) and the live view image $P_{Live}$ (live view mode) with a simple operation on the medical instrument 40 through the trocar 20 and safely perform the technique. Further, since the operator may switch between the simulation image $P_{sim1}$ (simulation mode) and the live view image $P_{Live}$ (live view mode) with a simple operation on the medical instrument 40 through the trocar 20, check and evaluation may be performed by all team members before surgery. Thus, it is possible to further increase the efficiency of the technique. Further, the operator may not bring the medical instrument 40 into the second state unless the operator strongly inserts the medical instrument 40 into the trocar 20. Thus, the safety may be increased. On the other hand, when the control unit 87 determines that the medical instrument 40 is not in the second state (Step S110: No), the medical observation system 1 shifts to step S109 (continues the simulation mode). Accordingly, the simulation image $P_{sim1}$ is displayed only when the medical instrument 40 is in the first state where the medical instrument 40 is located inside the trocar 20. Thus, it is possible to prevent contact with the surgical part of the subject $O_1$.

According to the first embodiment described above, the control unit 87 causes, based on a detection result of at least one trocar 20 into which the medical instrument 40 grasped by the operator is inserted, the at least one trocar 20 being capable of detecting the first state and the second state, the first state and the second state indicating the insertion state of the medical instrument 40 into the subject $O_1$, the display device 70 to display at least one of the live view image generated by capturing an image of the observation object inside the subject $O_1$ and the simulation image of the observation object inside the subject $O_1$, the simulation image being previously acquired. Thus, it is possible to support the operator during surgery without disturbing the operator during the surgery and perform surgery regardless of the experience of the operator.

Further, according to the first embodiment, when the trocar 20 detects that the medical instrument 40 is in the second state, the control unit 87 causes the display device 70 to display the live view image $P_{Live}$. Thus, the operator may perform procedures with the grasped medical instrument 40, 50 while watching the live view image $P_{Live}$.

Further, according to the first embodiment, when the trocar 20 detects that the medical instrument 40 is in the first state, the control unit 87 causes the display device 70 to display at least one of the live view image $P_{Live}$ and the simulation image $P_{sim1}$. Thus, the operator may smoothly switch between the live view image $P_{Live}$ and the simulation image $P_{sim1}$ while grasping the medical instrument 40 and without using another switch or another medical instrument.

Further, according to the first embodiment, the control unit 87 causes the display device 70 to display the medical instrument image corresponding to the medical instrument in a superimposed manner on the simulation image $P_{sim1}$ based on medical instrument information about the medical instrument 40 detected by the trocar 20. Thus, it is possible to intuitively grasp the positional relationship between the object on which procedures are performed and the medical instrument 40.

Further, according to the first embodiment, the control unit 87 controls the display mode of the medical instrument image and the simulation image $P_{sim1}$ based on details of an operation of the operator on the medical instrument 40.

Thus, the simulation may be performed through an operation with a feeling similar to an actual feeling.

Further, according to the first embodiment, when switching from the live view image $P_{Live}$ to the simulation image $P_{sim1}$, the control unit 87 causes the display device 70 to display the simulation image $P_{sim1}$ with the position of the organ included in the simulation image $P_{sim1}$ aligned with the position of the organ included in the live view image $P_{Live}$ based on the estimation result of the estimation unit 84. Thus, it is possible to switch from the live view image $P_{Live}$ to the simulation image $P_{sim1}$ without a sense of incongruity and also prevent loss sight of an organ included in the current observation visual field.

Further, according to the first embodiment, when the medical instrument 40 is in the first state, the control unit 87 causes the display device 70 to display the live view image $P_{Live}$ reduced in size and superimposed on the simulation image $P_{sim1}$. Thus, it is possible to perform simulation while making comparison between the simulation image $P_{sim1}$ and the live view image $P_{Live}$.

Further, according to the first embodiment, when switching from the live view image $P_{Live}$ to the simulation image $P_{sim1}$, the control unit 87 causes the display device 70 to output a warning. Thus, the operator may intuitively grasp the switch from the live view image $P_{Live}$ to the simulation image $P_{sim1}$.

Further, according to the first embodiment, the control unit 87 causes the display device 70 to display the simulation image $P_{sim2}$ with the observation object rotated in at least one of the horizontal direction and the vertical direction based on the insertion amount of the medical instrument 40, 50 into the insertion portion 271 of the trocar 20 and the rotation amount of the medical instrument 40, 50 which rotate about the insertion portion 271 of the trocar 20, the insertion amount and the rotation amount being detected by the trocar 20. This enables the operator to shift the simulation image to a desired view point merely by operating the medical instrument 40, 50.

Further, according to the first embodiment, the control unit 87 causes the display device 70 to display, in a superimposed manner on the live view image $P_{Live}$ displayed by the display device 70, the distance information $B_1$ including the optimum distance between the observation object and the distal end of the medical imaging device 30 which captures an image of the observation object of the subject $O_1$ in observation of fluorescence of the observation object of the subject $O_1$ based on the distance between the distal end of the medical imaging device 30 and the observation object of the subject $O_1$. This enables the operator to reliably prevent false positive or false negative by observing the current distance $K_1$ included in the distance information $B_1$ and the fluorescence emission amount from the observation object even with the emission amount of fluorescence that looks different depending on the distance between the observation object and the distal end of the medical imaging device 30.

Second Embodiment

Next, a second embodiment will be described. The second embodiment has the same configuration as the medical observation system 1 according to the first embodiment described above and differs from the first embodiment in a process to be executed. Specifically, in the above first embodiment, the display device 70 displays at least one of the live view image and the simulation image based on the detection result of one trocar 20. On the other hand, in the second embodiment, the display device 70 displays at least one of the live view image and the simulation image based on each of detection results of two trocars. Hereinbelow, a process executed by a medical observation system according to the second embodiment will be described. Note that elements same as those of the medical observation system 1 according to the above first embodiment are designated by the same reference signs as those in the first embodiment to omit detailed description thereof.

Process of Medical Observation System

Figure 13:
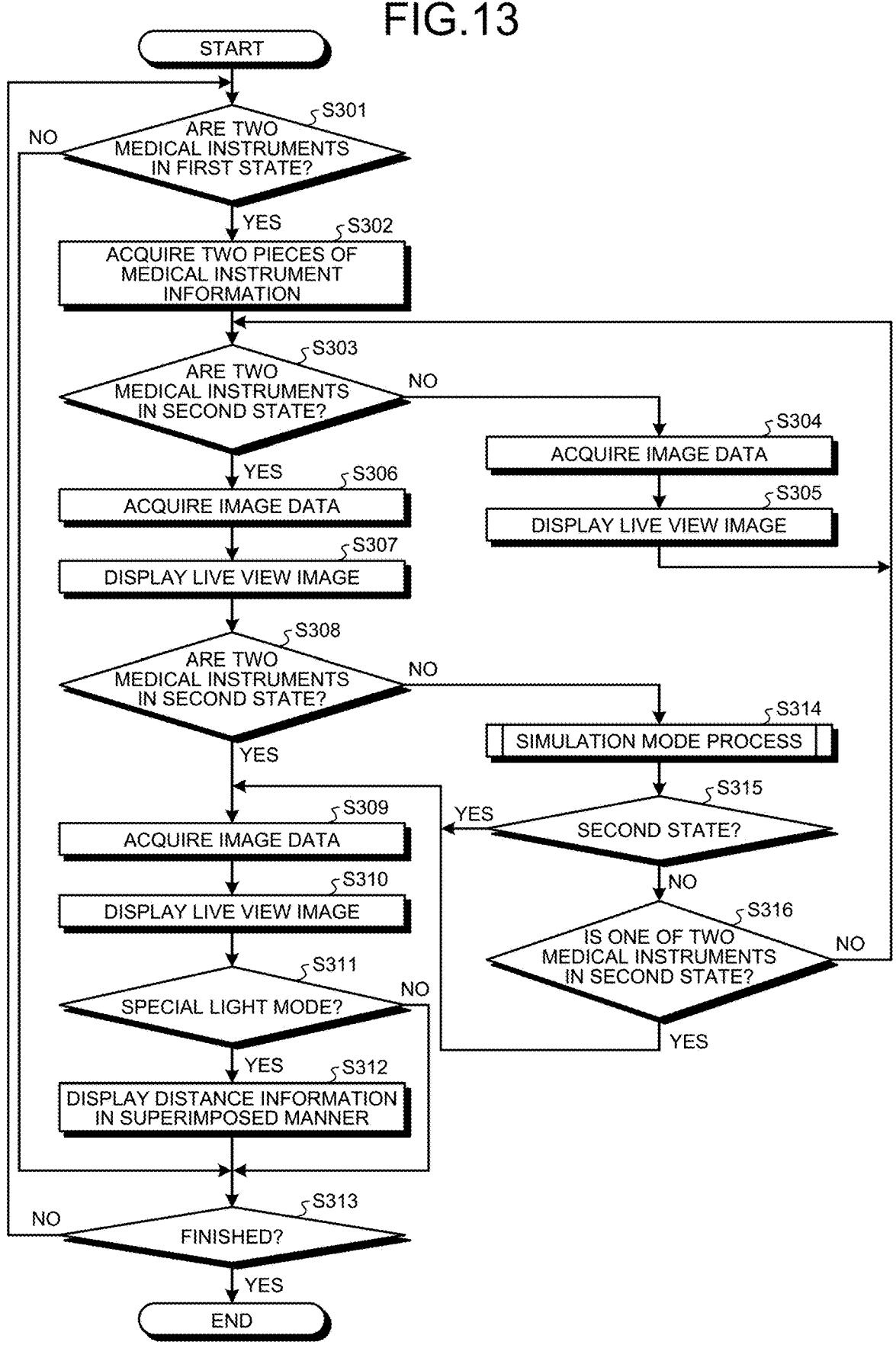
FIG. 13 is a flowchart illustrating an outline of a process executed by a medical observation system according to a second embodiment.

FIG. 13 is a flowchart illustrating a process executed by a medical observation system 1 according to the second embodiment.

As illustrated in FIG. 13, the control unit 87 first determines whether the two medical instruments 40, 50 are in the first state based on detection results detected by the first detection units 21 of the two trocars 20L, 20R. Specifically, the control unit 87 determines whether a detection result indicating that the insertion of the medical instrument 40 or the medical instrument 50 has been detected has been input from each of the first detection units 21 of the two trocars 20L, 20R. When the control unit 87 determines that the two medical instruments 40, 50 are in the first state (Step S301: Yes), the medical observation system 1 shifts to Step S302 (described below). On the other hand, when the control unit 87 determines that the two medical instruments 40, 50 are not in the first state (Step S301: No), the medical observation system 1 shifts to Step S313 (described below).

In step S302, the control unit 87 acquires type information of each of the medical instruments 40, 50 acquired by the acquisition units 23 of the two trocars 20L, 20R.

Then, the control unit 87 determines whether the two medical instruments 40, 50 are in the second state based on detection results detected by the second detection units 22 of the two trocars 20L, 20R (Step S303). Specifically, the control unit 87 determines whether a detection result indicating that the insertion of the medical instrument 40 or the medical instrument 50 has been detected has been input from each of the second detection units 22 of the two trocars 20L, 20R. When the control unit 87 determines that the two medical instruments 40, 50 are in the second state (Step S303: Yes), the medical observation system 1 shifts to step S306 (described below). On the other hand, when the control unit 87 determines that the two medical instruments 40, 50 are not in the second state (Step S303: No), the medical observation system 1 shifts to step S304 (described below).

In step S304, the control unit 87 acquires, via the first communication unit 81, image data generated by the medical imaging device 30. In this case, the control unit 87 causes the first communication unit 81 to output the image data to the image processing unit 82.

Then, the control unit 87 causes the image processing unit 82 to perform image processing on the image data acquired by the first communication unit 81 and output the image data to the display device 70 to cause the display device 70 to display a live view image based on the image data (e.g., refer to the live view image $P_{Live}$ in FIG. 6) (Step S305). After Step S305, the medical observation system 1 returns to Step S303 described above.

In Step S306, the control unit 87 acquires, via the first communication unit 81, image data generated by the medical imaging device 30.

Then, the control unit 87 causes the image processing unit 82 to perform image processing on the image data acquired by the first communication unit 81 and output the image data to the display device 70 to cause the display device 70 to display a live view image (Step S307).

Then, the control unit 87 determines whether the two medical instruments 40, 50 are in the second state based on detection results detected by the second detection units 22 of the two trocars 20L, 20R (Step S308). When the control unit 87 determines that the two medical instruments 40, 50 are in the second state (Step S308: Yes), the medical observation system 1 shifts to step S309 (described below). On the other hand, when the control unit 87 determines that the two medical instruments 40, 50 are not in the second state (Step S308: No), the medical observation system 1 shifts to step S314 (described below).

In Step S309, the control unit 87 acquires, via the first communication unit 81, image data generated by the medical imaging device 30.

Then, the control unit 87 causes the image processing unit 82 to perform image processing on the image data acquired by the first communication unit 81 and output the image data to the display device 70 to cause the display device 70 to display a live view image (Step S310). Accordingly, an operator performs procedures with the two medical instruments 40, 50 inserted in the subject $O_1$ while watching the live view image.

Steps S311 to S315 respectively correspond to Steps S106 to S110 in FIG. 5 described above.

In step S316, the control unit 87 determines whether one of the two medical instruments 40, 50 is in the second state based on detection results detected by the second detection units 22 of the two trocars 20L, 20R. When the control unit 87 determines that one of the two medical instruments 40, 50 is in the second state (Step S316: Yes), the medical observation system 1 shifts to Step S309. This enables the operator to perform procedures on the subject $O_1$ in the actual visual field because the control unit 87 causes the display device 70 to display the live view image (shifts to the live view mode) also when one of the two medical instruments 40, 50 is in the second state. In this case, the control unit 87 may cause the display device 70 to issue a warning indicating that the displayed image is not the simulation image with, for example, sound and text. On the other hand, when the control unit 87 determines that one of the two medical instruments 40, 50 is not in the second state (Step S316: No), the medical observation system 1 shifts to Step S303.

According to the second embodiment described above, the control unit 87 causes, based on detection results of the two trocars 20 into which the two medical instruments 40, 50 grasped by the operator are inserted, the two trocars 20 being capable of detecting the first state and the second state, the first state and the second state indicating the insertion states of the medical instruments 40, 50 into the subject $O_1$, the display device 70 to display at least one of the live view image obtained by capturing an image of the observation object inside the subject $O_1$ and the simulation image of the observation object inside the subject $O_1$, the simulation image being previously acquired. Thus, it is possible to support the operator during surgery without disturbing the operator during the surgery.

Further, according to the second embodiment, when the two trocars 20 detect that the two medical instruments 40, 50 are in the second state, the control unit 87 causes the display device 70 to display the live view image $P_{Live}$. Thus, the operator may perform procedures with the grasped medical instruments 40, 50 while watching the live view image $P_{Live}$.

Further, according to the second embodiment, when the two trocars 20 detect that the two medical instruments 40, 50 are in the first state, the control unit 87 causes the display device 70 to display at least the simulation image $P_{sim1}$.

Thus, the operator may smoothly switch between the live view image $P_{Live}$ and the simulation image $P_{sim1}$ while grasping the medical instruments 40, 50 and without using another switch or another medical instrument.

Further, in the second embodiment, only when the two trocars 20 detect that the two medical instruments 40, 50 are in the first state, the control unit 87 causes the display device 70 to display at least the simulation image $P_{sim1}$. Thus, the operator may smoothly switch between the live view image $P_{Live}$ and the simulation image $P_{sim1}$ while grasping the medical instruments 40, 50.

Other Embodiments

Variations may be formed by appropriately combining a plurality of elements disclosed in the medical observation systems according to the first and second embodiments of the present disclosure. For example, some elements may be deleted from all the elements described in the medical observation systems according to the embodiments of the present disclosure. Further, the elements described in the medical observation systems according to the first and second embodiments of the present disclosure may be appropriately combined.

Further, in the medical observation systems according to the first and second embodiments of the present disclosure, the "unit" described above may be read as "means" or "circuit". For example, the control unit may be read as control means or a control circuit.

Further, a program to be executed by the medical observation systems according to the first and second embodiments of the present disclosure is provided as file data in an installable or executable format recorded on a computer-readable recording medium such as a CD-ROM, a flexible disk (FD), a CD-R, a Digital Versatile Disk (DVD), a USB medium, or a flash memory.

Further, a program to be executed in the medical observation systems according to the first and second embodiments of the present disclosure may be stored on a computer connected to a network such as the Internet and may be downloaded via the network to be provided.

Note that although, in the description of the flowcharts in this specification, the order of processes between the steps is specified using expressions such as "first", "after", and "then", the order of processes necessary to implement the present disclosure is not uniquely defined by these expressions. That is, the order of the processes in the flowcharts described in this specification may be changed within a consistent range.

Although some of embodiments of the present application have been described in detail with reference to the drawings, these embodiments are merely examples, and the present disclosure may be implemented in, in addition to the modes described in the present disclosure, other embodiments with various modifications and improvements applied based on knowledges of those skilled in the art.

Note that the present technique may also include configurations as described below.

(1)

A medical image processing apparatus including
a control unit configured to cause, based on a detection result of at least one trocar into which a medical instrument is inserted, the at least one trocar being configured to detect a first state and a second state, the first state and the second state indicating an insertion state of the medical instrument into a subject, a display device to display at least one of a first image generated by capturing an image of an observation object inside the subject and a second image of the observation object inside the subject, the second image being previously acquired.

(2)
The medical image processing apparatus according to (1), wherein
the first state is a state where the medical instrument is located inside the at least one trocar, and
the second state is a state where at least a part of the medical instrument is inserted and exposed into the subject via the at least one trocar.

(3)
The medical image processing apparatus according to (1) or (2), wherein the control unit is configured to
cause the display device to display the first image when the medical instrument is in the second state, and
cause the display device to display at least the second image when the medical instrument is in the first state.

(4)
The medical image processing apparatus according to any one of (1) to (3), wherein the control unit is configured to cause the display device to display a medical instrument image corresponding to the medical instrument in a superimposed manner on the second image based on medical instrument information about the medical instrument detected by the at least one trocar.

(5)
The medical image processing apparatus according to (4), wherein the control unit is configured to control a display mode of the medical instrument image and the second image based on details of an operation of an operator on the medical instrument.

(6)
The medical image processing apparatus according to (5), further including
an estimation unit configured to estimate a position of an organ included in the first image and a position of the organ included in the second image, wherein
in a case where switching from the first image to the second image, the control unit is configured to cause the display device to display the second image with the position of the organ included in the second image aligned with the position of the organ included in the first image based on an estimation result of the estimation unit.

(7)
The medical image processing apparatus according to any one of (1) to (6), wherein the control unit is configured to cause the display device to display the first image and the second image in parallel or causes the display device to display the first image reduced in size and superimposed on the second image.

(8)
The medical image processing apparatus according to any one of (1) to (7), wherein in a case where switching from the first image to the second image, the control unit is configured to cause the display device to output a warning.

(9)
The medical image processing apparatus according to any one of (1) to (8), wherein
the at least one trocar includes two trocars,
the display device is configured to display the first image in a case where each of the two trocars detects the second state, and
the display device is configured to display at least the second image in a case where each of the two trocars detects the first state.

(10)
The medical image processing apparatus according to any one of (1) to (9), wherein
the first image is a live view image generated by continuously capturing an image of the observation object inside the subject, and
the second image is a simulation image of the observation object inside the subject.

(11)
The medical image processing apparatus according to any one of (1) to (9), wherein
the first image is a live view image generated by continuously capturing an image of the observation object inside the subject, and
the second image is medical information about the observation object inside the subject.

(12)
The medical image processing apparatus according to (5), wherein the control unit is configured to cause the display device to display the second image with the observation object rotated in at least one of a horizontal direction and a vertical direction based on at least one of a rotation amount of the medical instrument configured to rotate about an insertion portion of the at least one trocar and an insertion amount of the medical instrument into the insertion portion of the at least one trocar, the rotation amount and the insertion amount being detected by the at least one trocar.

(13)
The medical image processing apparatus according to (1), wherein the control unit is configured to cause, based on a distance between the observation object and a distal end of a medical imaging device configured to capture an image of the observation object, the display device to display distance information including an optimum distance between the observation object and the distal end in observation of fluorescence of the observation object.

(14)
A trocar including:
a main body having a tubular shape and including a hole into which a medical instrument is insertable from outside;
a first detection unit disposed in an insertion direction of the hole and configured to detect, as a first state, a position of the medical instrument inserted in the hole; and
a second detection unit disposed in the insertion direction of the hole at such a position that an insertion distance of the medical instrument is longer than an insertion position of the medical instrument in a case of being detected by the first detection unit and configured to detect, as a second state, a position of the medical instrument inserted in the hole.

(15)
The trocar according to (14), further including an acquisition unit configured to acquire medical instrument information about the medical instrument on the medical instrument inserted into the hole.

(16)
The trocar according to (14) or (15), wherein
each of the first detection unit and the second detection unit includes:
a fitting member projectable to the hole and fittable with the medical instrument;

a biasing member configured to bias the fitting member from an outer edge of the hole toward a center of the hole; and a pressure sensor configured to detect a biasing state of the biasing member and output a result of the detection to outside.

(17)

The trocar according to (14) or (15), wherein the first state is a state where the medical instrument is located inside the trocar, and the second state is a state where at least a part of the medical instrument is inserted and exposed into a subject through the trocar.

(18)

A medical observation system including:

an imaging unit configured to generate a first image by capturing an image of an observation object of a subject;

a recording unit configured to record a second image based on three-dimensional image data or a two-dimensional image data of the observation object of the subject, the second image being previously acquired;

a display device capable of displaying the first image and the second image;

at least one trocar into which a medical instrument is inserted, the at least one trocar being configured to detect a first state and a second state, the first state and the second state indicating an insertion state of the medical instrument into the subject; and a control unit configured to cause the display device to display at least one of the first image and the second image based on a detection result of the at least one trocar.

(19)

An image processing method including causing, based on a detection result of at least one trocar into which a medical instrument is inserted, the at least one trocar being configured to detect a first state and a second state, the first state and the second state indicating an insertion state of the medical instrument into a subject, a display device to display at least one of a first image generated by capturing an image of an observation object inside the subject and a second image of the observation object inside the subject, the second image being previously acquired.

(20)

A non-transitory computer-readable recording medium on which an executable program is recorded, the program causing a processor to execute causing a display device to display at least one of a first image generated by capturing an image of an observation object inside a subject and a previously acquired second image of the observation object inside the subject based on a detection result of at least one trocar into which a medical instrument is inserted, the at least one trocar being configured to detect a first state and a second state, the first state and the second state indicating an insertion state of the medical instrument into the subject.

The present disclosure achieves an effect capable of supporting an operator during surgery without disturbing the operator during the surgery.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing apparatus comprising a circuit configured to output, based on a detection result of at least one trocar into which a medical instrument is inserted, the at least one trocar including a first detector configured to detect a first state and a second detector configured to detect a second state, the first state and the second state indicating an insertion state of the medical instrument into the at least one trocar and a subject, to a display, at least one of a first image generated by capturing a live image of an observation object inside the subject and a second image that is a simulation image of the observation object inside the subject, the second image being previously acquired, wherein, in response to the first state being detected, output at least the second image, and in response to the second state being detected, only output the first image of the first and second images.

2. The medical image processing apparatus according to claim 1, wherein the first state is a state where the medical instrument is located at a position inside the at least one trocar, and the second state is a state where at least a part of the medical instrument extends through the at least one trocar and exposed into the subject through the at least one trocar.

3. The medical image processing apparatus according to claim 1, wherein the circuit is configured to cause the display to display a medical instrument image corresponding to the medical instrument in a superimposed manner on the second image based on medical instrument information about the medical instrument detected by the at least one trocar.

4. The medical image processing apparatus according to claim 3, wherein the circuit is configured to control a display mode of the medical instrument image and the second image based on details of an operation of an operator on the medical instrument.

5. The medical image processing apparatus according to claim 4, wherein the circuit is configured to output to the display the second image with the observation object rotated in at least one of a horizontal direction and a vertical direction based on at least one of a rotation amount of the medical instrument configured to rotate about an insertion portion of the at least one trocar and an insertion amount of the medical instrument into the insertion portion of the at least one trocar, the rotation amount and the insertion amount being detected by the at least one trocar.

6. The medical image processing apparatus according to claim 4, wherein, in response to the at least one trocar switching from the second state to the first state, the circuit is configured to estimate a position of an organ included in the first image and a position of the organ included in the second image, and cause the display to display the second image with the position of the organ included in the second image aligned with the position of the organ included in the first image based on the estimate.

7. The medical image processing apparatus according to claim 1, wherein the circuit is configured to, when the first state is detected, cause the display to display the first image and the second image in parallel or to display the first image reduced in size and superimposed on the second image.

8. The medical image processing apparatus according to claim 1, wherein
in response to the at least one trocar switching from the second state to the first state, the circuit is configured to cause the display to output a warning.

9. The medical image processing apparatus according to claim 1, wherein
the at least one trocar comprises two trocars, and
the circuit is configured to control the display to
display the first image in a case where each of the two trocars detects the second state, and
display at least the second image in a case where each of the two trocars detects the first state.

10. The medical image processing apparatus according to claim 1, wherein the circuit is configured to output to the display, based on a distance between the observation object and a distal end of a medical imaging device configured to capture an image of the observation object, distance information including an optimum distance between the observation object and the distal end in observation of fluorescence of the observation object.

11. A medical observation system comprising:
an image sensor configured to generate a first image by capturing a live image of an observation object of a subject;
a memory configured to store a second image based on three-dimensional image data or a two-dimensional image data of the observation object of the subject, the second image being previously acquired;
a display;
at least one trocar into which a medical instrument is inserted, the at least one trocar including a first detector configured to detect a first state and a second detector configured to detect a second state, the first state and the second state indicating an insertion state of the medical instrument into the at least one trocar and the subject; and
a control circuit configured to output at least one of the first image and the second image to the display based on a detection result of the at least one trocar, wherein,
in response to the first state being detected, output at least the second image, and
in response to the second state being detected, output only the first image of the first and second images to the display.

12. An image processing method comprising
determining a state of at least one trocar into which a medical instrument is inserted, the at least one trocar including a first detector configured to detect a first state and a second detector configured to detect a second state, the first state and the second state indicating an insertion state of the medical instrument into the at least one trocar and a subject, and
controlling output to a display of at least one of a first image generated by capturing a live image of an observation object inside the subject and a second image of the observation object inside the subject, the second image being previously acquired, wherein
in response to the first state being detected, outputting at least the second image to the display, and
in response to the second state being detected, outputting only the first image of the first and second images to the display.

13. A non-transitory computer-readable recording medium on which an executable program is recorded, the program causing a processor to execute;

determining a state of at least one trocar into which a medical instrument is inserted, the at least one trocar including a first detector configured to detect a first state and a second detector configured to detect a second state, the first state and the second state indicating an insertion state of the medical instrument into the at least one trocar and a subject, and
controlling output to a display of at least one of a first image generated by capturing a live image of an observation object inside the subject and a second image of the observation object inside the subject, the second image being previously acquired, wherein
in response to the first state being detected, outputting at least the second image, and
in response to the second state being detected, outputting only the first image of the first and second images to the display.

14. The non-transitory computer-readable recording medium according to claim 13, wherein the program causes the processor to control the display to display a medical instrument image corresponding to the medical instrument in a superimposed manner on the second image based on medical instrument information about the medical instrument detected by the at least one trocar.

15. The non-transitory computer-readable recording medium according to claim 14, wherein the program causes the processor to control a display mode of the medical instrument image and the second image based on details of an operation of an operator on the medical instrument.

16. The non-transitory computer-readable recording medium according to claim 15, wherein the program causes the processor to, in response to the at least one trocar switching from the second state to the first state,
estimate a position of an organ included in the first image and a position of the organ included in the second image, and
control the display to display the second image with the position of the organ included in the second image aligned with the position of the organ included in the first image based on the estimate.

17. The non-transitory computer-readable recording medium according to claim 15, wherein the program causes the processor to output to the display the second image with the observation object rotated in at least one of a horizontal direction and a vertical direction based on at least one of a rotation amount of the medical instrument configured to rotate about an insertion portion of the at least one trocar and an insertion amount of the medical instrument into the insertion portion of the at least one trocar, the rotation amount and the insertion amount being detected by the at least one trocar.

18. The non-transitory computer-readable recording medium according to claim 13, wherein the program causes the processor to control, when the first state is detected, the display to display the first image and the second image in parallel or to display the first image reduced in size and superimposed on the second image.

19. The non-transitory computer-readable recording medium according to claim 13, wherein the program causes the processor to, in response to the at least one trocar switching from the second state to the first state, cause the display to output a warning.

20. The non-transitory computer-readable recording medium according to claim 13, wherein the at least one trocar includes two trocars, the program causes the processor to, control the display to display the first image in a case where each of the two trocars detects the second state, and
display at least the second image in a case where each of the two trocars detects the first state.

\* \* \* \* \*